United States Patent
Oroskar et al.

(10) Patent No.: US 10,857,483 B2
(45) Date of Patent: Dec. 8, 2020

(54) ADSORBENT FOR CHROMATOGRAPHIC SEPARATION OF PROTEINS

(71) Applicant: OROCHEM Technologies, Inc., Naperville, IL (US)

(72) Inventors: Anil R Oroskar, Oak Brook, IL (US); Babu Siddegowda Antharavally, Caledonia, IL (US); Anantha Krishna Mallia, Rockford, IL (US)

(73) Assignee: Orochem Technologies Inc., Naperville, IL (US)

( * ) Notice: Subject to any disclaimer, the term of this patent is extended or adjusted under 35 U.S.C. 154(b) by 0 days.

(21) Appl. No.: 15/818,727

(22) Filed: Nov. 20, 2017

(65) Prior Publication Data

US 2018/0071655 A1 Mar. 15, 2018

Related U.S. Application Data

(62) Division of application No. 14/848,196, filed on Sep. 8, 2015, now Pat. No. 9,821,249.

(51) Int. Cl.

| | |
|---|---|
| *B01D 15/36* | (2006.01) |
| *B01D 15/18* | (2006.01) |
| *C07K 14/415* | (2006.01) |
| *C07K 14/47* | (2006.01) |
| *B01J 41/05* | (2017.01) |
| *C07K 1/14* | (2006.01) |
| *C12N 9/88* | (2006.01) |
| *B01J 41/14* | (2006.01) |
| *B01J 41/20* | (2006.01) |

(52) U.S. Cl.
CPC ......... *B01D 15/363* (2013.01); *B01D 15/185* (2013.01); *B01D 15/1835* (2013.01); *B01J 41/05* (2017.01); *B01J 41/14* (2013.01); *B01J 41/20* (2013.01); *C07K 1/145* (2013.01); *C07K 14/415* (2013.01); *C07K 14/47* (2013.01); *C12N 9/88* (2013.01); *C12Y 401/01039* (2013.01)

(58) Field of Classification Search
None
See application file for complete search history.

(56) References Cited

U.S. PATENT DOCUMENTS

| | | | |
|---|---|---|---|
| 3,472,840 A | 10/1969 | Stone et al. | |
| 4,175,183 A | 11/1979 | Ayers | |
| 5,731,259 A | 3/1998 | Palumbo et al. | |
| 5,780,616 A | 7/1998 | Fornasari et al. | |
| 6,911,483 B2 | 6/2005 | Ayers et al. | |
| 2004/0241878 A1 | 12/2004 | Thommes et al. | |
| 2006/0254737 A1* | 11/2006 | Anderson | C08B 31/003 162/175 |
| 2009/0105515 A1 | 4/2009 | Winter et al. | |
| 2010/0059440 A1* | 3/2010 | Rudstedt | B01D 67/0093 210/651 |
| 2010/0176058 A1 | 7/2010 | Bryntesson et al. | |
| 2014/0179933 A1 | 6/2014 | Oroskar et al. | |
| 2014/0275518 A1 | 9/2014 | Oroskar et al. | |
| 2015/0203789 A1 | 7/2015 | Oroskar et al. | |

OTHER PUBLICATIONS

Diamantoglou et al. Erlenbach, D-8765, Fed. Rep. Ger. Papier (Bingen, Germany) (1988), 42(12), 690-6 (Abstract) (Year: 1988).*
Kuniak. Cellulose Chemistry and Technology (1974), 8(3), 255-62 (Abstract) (Year: 1974).*
Antal et al., "Preparation of microcrystalline cellulose aminoderivatives", Carbohydrate Polymers, 1992, pp. 167-169, vol. 19, Issue 3, Elsevier Ltd., US (Abstract).
Erlenbach et al., Papier (Bingen, Germany) (1988), 42(12), 690-6.
Gong et al., J Chromatogr A. Oct. 10, 2014;1363:242-9. Epub Jul. 7, 2014.
Lay et al., "Continuous Radial Flow Chromatography of Proteins", Food and Bioproducts Processing, vol. 84, No. C1, pp. 78-83 (2006).
International Search Report and the Written Opinion in corresponding International application PCT/US2016/050337 (dated Dec. 22, 2016).

* cited by examiner

*Primary Examiner* — Christian L Fronda
(74) *Attorney, Agent, or Firm* — Leydig, Voit & Mayer, Ltd.

(57) ABSTRACT

Disclosed is a continuous process for separating or extracting proteins from a low grade mixture of a protein of interest, other proteins, impurities, and salts in a continuous simulated moving bed separation process. The invention provides for direct extraction of heme protein and plant protein from a crude mixture of such proteins, other proteins, impurities and salts using the chromatographic technique of simulated moving bed (SMB) continuous chromatography. The SMB process combines the steps of feed loading, adsorbent washing, product elution, adsorbent regeneration, and adsorbent equilibration. The novel strong anion exchange resin adsorbent is a quaternary amine cross-linked microcellulose wherein the microcellulose is cross-linked with epichlorohydrin and the quaternary amine is 2,3-epoxypropyltrimethyl-ammonium chloride which exhibits selective adsorption of proteins and complete regeneration. Purified protein separated in this manner may provide human health benefits by providing greater medicinal and nutrition opportunities from low quality protein sources.

12 Claims, 16 Drawing Sheets

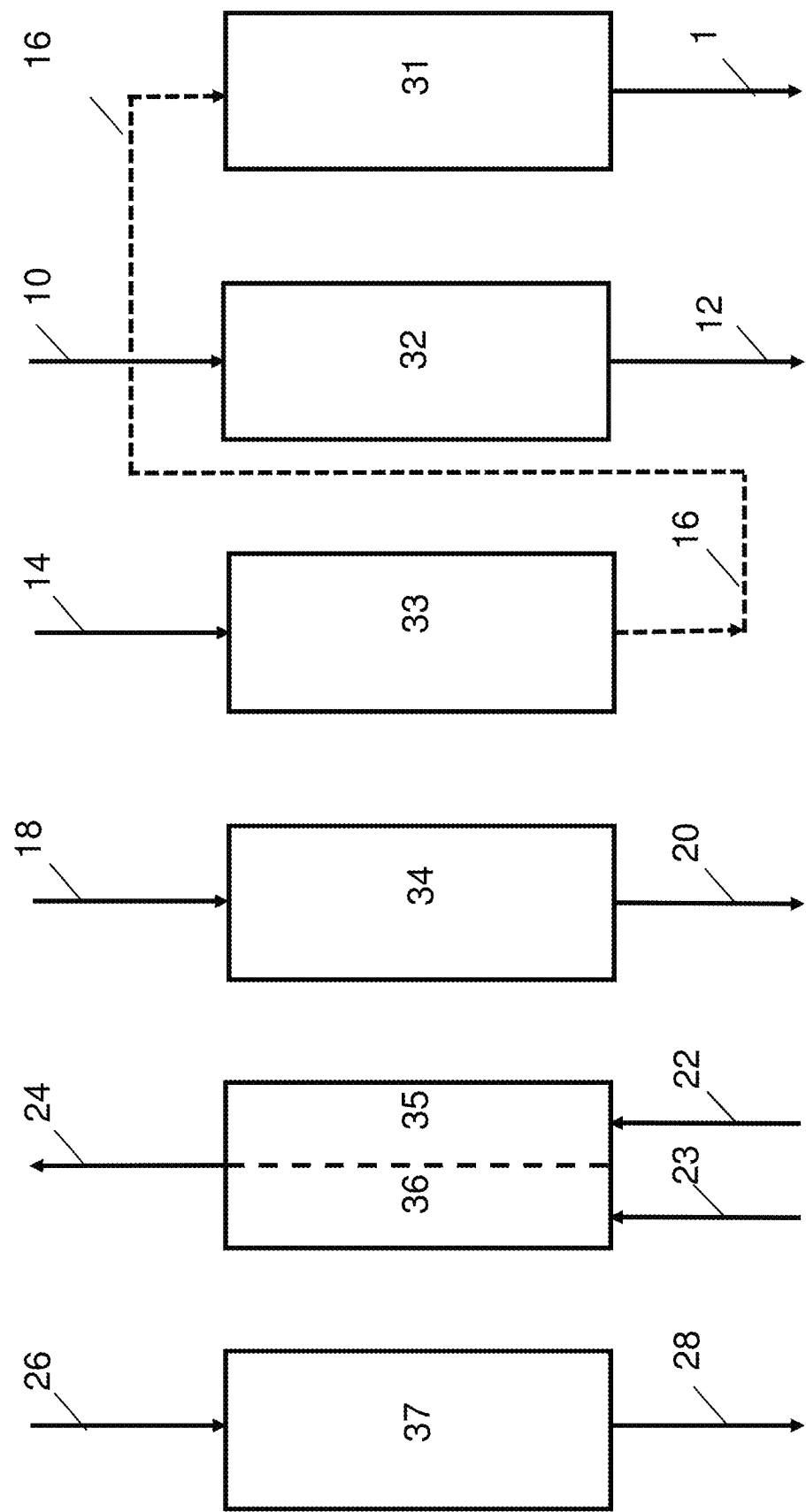

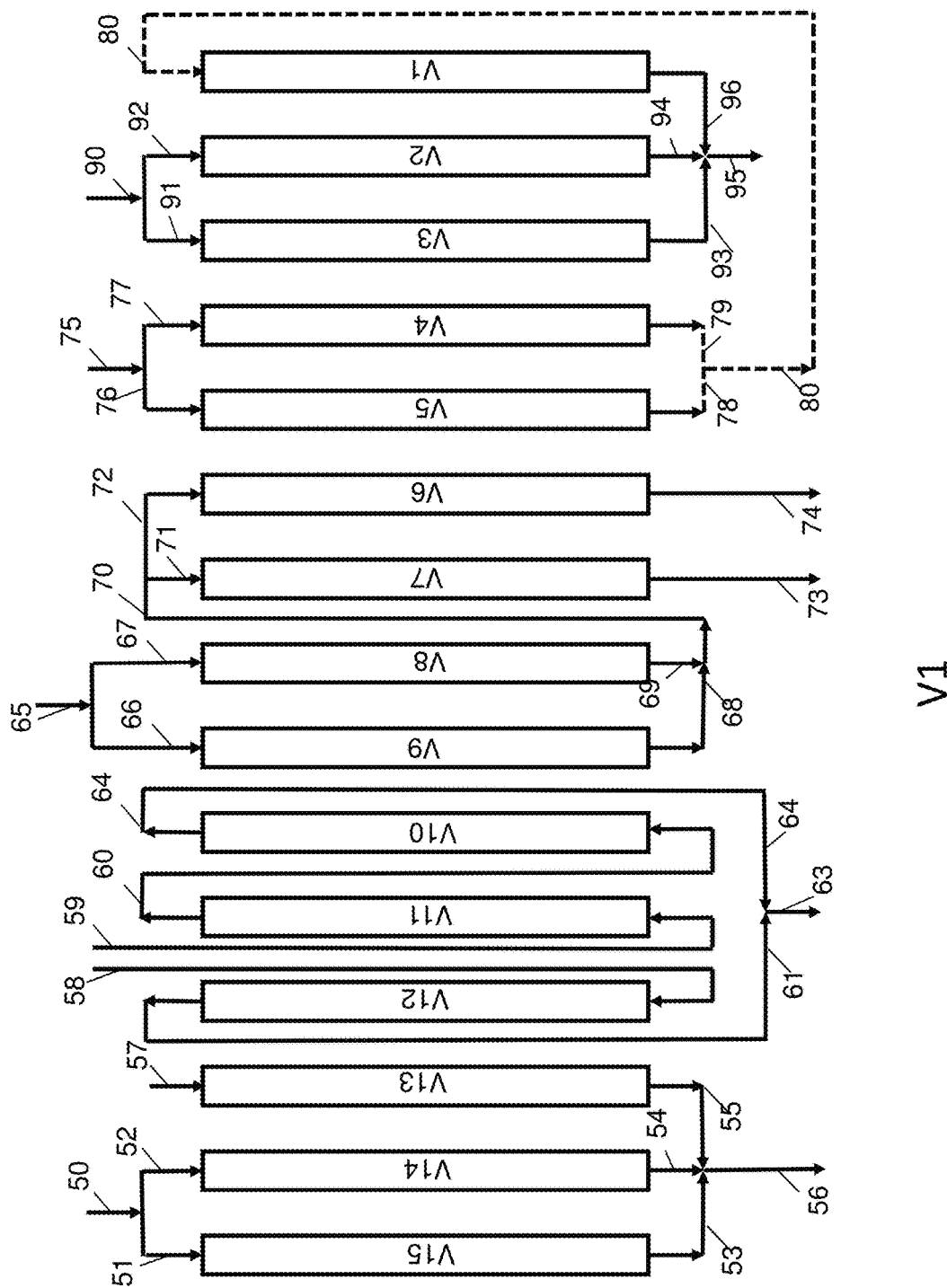

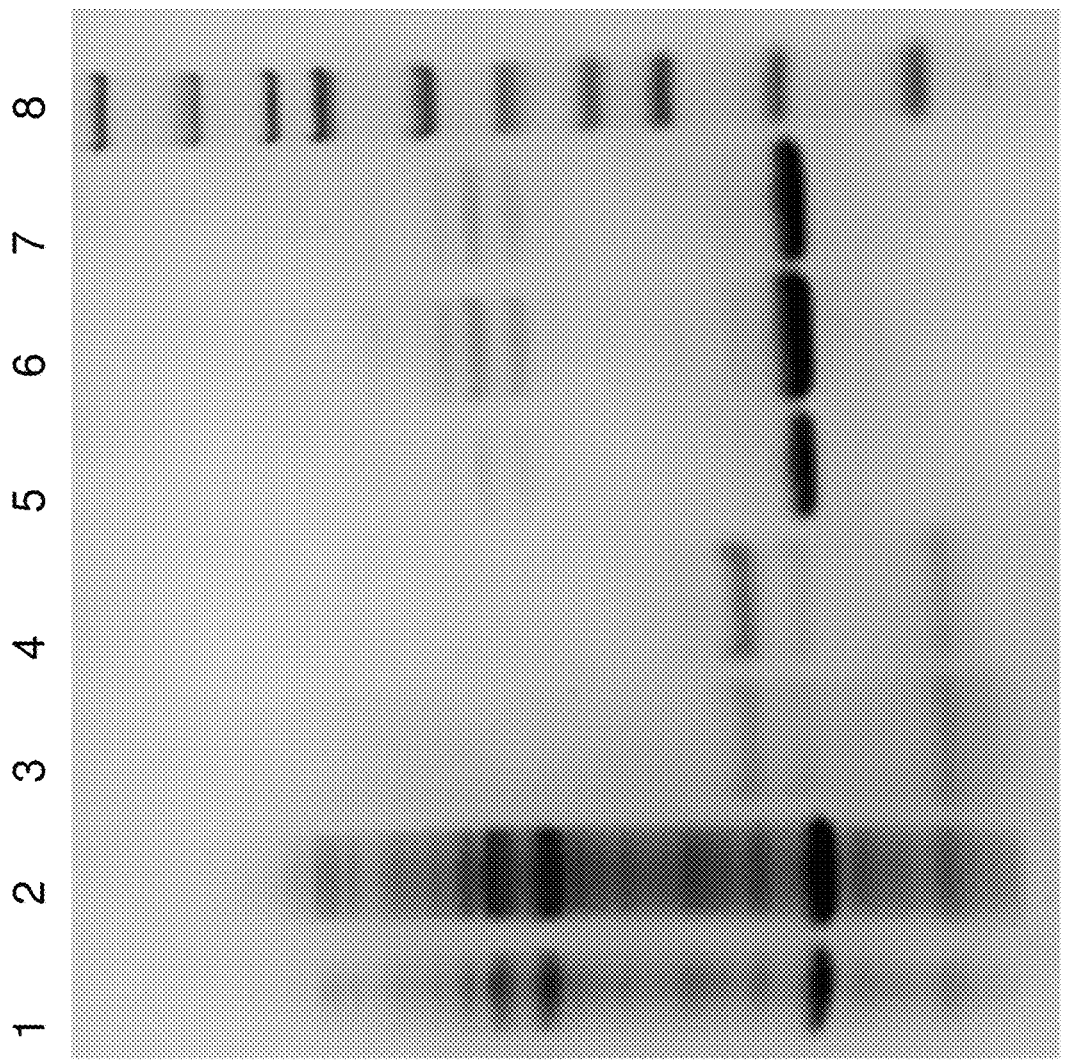

ADSORBENT FOR CHROMATOGRAPHIC SEPARATION OF PROTEINS

CROSS REFERENCE TO RELATED APPLICATIONS

The present application claims benefit from U.S. Ser. No. 14/848,196 filed Sep. 8, 2015, which is hereby incorporated by reference in its entirety as if fully restated herein.

FIELD OF THE INVENTION

The invention relates to a continuous method for separating or extracting proteins from a low grade mixture of proteins and impurities in a continuous direct separation process. More particularly, the invention provides for direct extraction of a protein directly from a mixture of proteins and impurities derived from plant protein extract using chromatographic technique of simulated moving bed continuous chromatography, employing a selective adsorbent as the stationary phase adsorbent, wherein the selective adsorbent is a strong anion exchange resin. Most specifically, the strong anion exchange resin has a backbone matrix comprising a cross linked styrene divinyl benzene polymer, a hydroxylated polymethacrylate polymer, or a cross linked microcrystalline cellulose resin. Purified protein separated in the continuous manner of the instant invention may provide human health benefits by providing greater medicinal and nutrition opportunities from low quality protein sources.

BACKGROUND

Proteins are important constituents of foods. Proteins are a major source of energy, and proteins contain essential amino-acids, such as lysine, tryptophan, methionine, leucine, isoleucine and valine, which are essential to human health. Proteins are the major structural components of many natural foods, and a particular protein in a food can determine the food structure or texture, e.g., tenderness of meat or fish products. Some individual proteins are used as food ingredients because they can improve appearance, texture or stability. Such individual proteins are employed as gelling agents, emulsifiers, foaming agents, and thickeners.

There is an increasing requirement for protein production in academic and industrial settings for a variety of applications like drug discovery, biopharmaceutical production, and the food industry. Currently, large-scale production strategies are capable of providing cell cultures or fermentation titres containing 25-50 wt % of the desired protein, and the remaining 50-75 percent impurities. Current applications require that essentially all impurities be removed from a highly purified protein product, and that the highly purified protein product can be produced in commercial quantities.

Heme protein refers to a metallo protein which contains a reduced iron atom, $Fe^{2+}$ in the center of a complex hydrophobic structure. Heme proteins play a role in critical physiological functions because the iron atom in heme protein make heme proteins responsive to molecules which can bind to divalent iron, such as oxygen, nitric oxide, carbon monoxide, and hydrogen sulfide. Hemoglobin and myoglobin are types of heme proteins which are essential for storing and transporting oxygen in mammals. Hemoglobin is also found in the root nodules of some plants. Leghemoglobin (legHb) occurs in the root nodules of leguminous plants, where it facilitates the diffusion of oxygen to symbiotic bacteriods in order to promote nitrogen fixation.

Plant proteins, such as Ribulose-1,5-bisphosphate carboxylase oxygenase, most commonly known by the shorter name RuBisCO, is an plant enzyme involved in the Calvin cycle that catalyzes the first major step of carbon fixation, a process by which atmospheric carbon dioxide is made available to organisms in the form of energy-rich molecules such as glucose. RuBisCO is very important in terms of biological impact, because it catalyzes the primary chemical reaction by which inorganic carbon permanently enters the biosphere. RuBisCO is also the most abundant protein in leaves, and is considered to be the most abundant protein on Earth.

Cellulose is the main component of higher plant cell walls and one of the most abundant organic compounds on earth. It can be derived from a number of sources using a number of techniques that are considered synthetic, and some that might be considered non-synthetic (natural). It is available in many forms for different functional purposes in food products. The three main forms of cellulose that have been considered for various uses are powdered cellulose, regenerated cellulose casing, and microcrystalline cellulose. Microcrystalline cellulose is purified, partially depolymerized cellulose. It is a fine, white, odorless crystalline powder which is insoluble in water, insoluble in dilute acids, insoluble in most organic solvents, and also insoluble in dilute sodium hydroxide solutions. Microcrystalline cellulose is primarily used in food to stabilize and improve the body, texture, and stability of food products.

Ion exchangers which have been used in separating whey proteins from whey protein containing solutions include both cation exchangers, particularly of the SP or SE (sulphonate) or CM (carboxymethyl) type, and anion exchangers, particularly of the QA (quaternary amino) or DEAE (diethylaminoethyl) type. In terms of the exchanger matrix itself, many insoluble matrices have been used, including cellulose, cross-linked dextran, cross-linked agarose, synthetic hydophilic polymers and inorganic materials coated with hydrophilic polymers. One matrix that has proved to be particularly useful in large scale separation and purification of whey proteins is regenerated cellulose which has been hydroxyalkylated and cross-linked. Ion exchangers prepared on this matrix are resistant to attrition, have high protein capacity, high flow properties and are available at relatively low cost.

Preparation of quaternized celluloses is known in the art, for example from U.S. Pat. No. 3,472,840 assigned to Union Carbide Corporation, which discloses cellulose derivatives, particularly cellulose ethers containing quaternary ammonium groups which are used in the many fields in which cellulose ethers cannot be employed.

U.S. Pat. No. 6,911,483 to Ayers et al. discloses an anion exchanger comprising a water insoluble, hydrophilic, water swellable, hydroxy($C_2$-$C_4$ alkylated and cross-linked regenerated cellulose, derivatized with quaternary amino (QA) groups. Ayers et al. discloses and claims that such anion exchangers have a level of substitution of the QA groups of 1.4 milliequivalents per dry gram of anion exchanger (meq/g) or greater. Anion exchangers are useful for separating proteins from protein-containing solutions, and particularly for adsorbing whey proteins from whey protein-containing solutions. Ayers et al. further differentiates such anion exchanger compositions based on regenerated cellulose from materials produced from microcrystalline cellulose with reference to Antal et al. Antal et. al. (Carbohydrate Polymers 19, 167-169, 1992) describe the optimization of the reaction of microcrystalline cellulose with the alkylating agents CHPTAC-(chloro-2-hydroxypropyl)trimethylammonium chloride) and 1,3-bis(3-chloro-2-hydroxy-propyl)imidazolium hydrogen sulfate in alkaline medium. Ayers et al. states that the maximum substitution level they [Antal et al.] were able to obtain with CHPTAC was 0.94 meq/g (mmol/g, millimoles per gram)), although the second reagent gave a product with 1.56 meq/g. No protein capacities are given and it is likely that the latter reagent, being bifunctional, would have introduced extensive crosslinking into the cellulose to the detriment of protein capacity. Furthermore, Ayers et al. states that microcrystalline cellulose is not a suitable matrix for repeated use on a large industrial scale.

Fibrous cellulose has been derivatized with quaternary ammonium groups to a high degree of substitution, DS of at least 0.5 (>2 meq/g), using a very large excess of alkylating reagent containing quaternary ammonium groups. The cellulose is either not crosslinked (1998 U.S. Pat. No. 5,731,259) or crosslinked (1998 U.S. Pat. No. 5,780,616). Preferably the alkylating reagent is used in 20:1 to 40:1 mole ratio of reagent to anhydroglucose units of cellulose. In the case of GTAC this amounts to 186-372 g of reagent per 10 g of cellulose used either in 5-8 repeated reactions or one large addition of the solid reagent with 30 mL of water. The products, described at one point as a jelly mass, are useful as superabsorbents for water and saline solutions in the field of hygenic-sanitary products such as diapers for babies. They are designed to be used once and then disposed of and are not at all suitable for repeated use day after day in a reactor or column bed where physical robustness against attrition, long life and high flow-through rates are required for anion exchangers processing protein solutions.

Processes are sought for the large scale separation and continuous purification of proteins, such as heme proteins and plant proteins, from mixtures of protein-containing solutions such as animal and vegetable derived protein extracts.

SUMMARY

The process of the present invention relates to the purification of proteins directly from mixtures of protein containing solutions using novel chromatographic techniques. More specifically, Applicant has developed a novel simulated moving bed separation process (SMB) series of adsorbent/desorbent combinations and SMB configurations to bring about the enrichment and purification of protein from mixtures of protein containing solutions directly from such mixtures without breaking down the protein and without extreme chemical and physical separation conditions such as heat or the use of supercritical pressure. Options for the SMB stationary phase adsorbent include strong anion exchange resin or a novel adsorbent based on microcrystalline cellulose. The novel SMB adsorbent developed for the SMB process of the invention comprises a cross-linked microcrystalline cellulose/quaternary amino (QA) anion exchanger as a stationary phase adsorbent in combination with a series of buffer desorbents to provide an enriched extract stream rich in purified protein, and a series of waste raffinate streams comprising impurities. A purified [DA1] protein product having a purity greater than 80 wt percent (e.g., 82, 83, 85 wt %) following solvent removal can be obtained.

In one embodiment, the invention is a process for the continuous extraction of heme protein from an aqueous protein mixture comprising heme protein, water, other proteins, contaminants and salts in of a continuous simulated moving bed (SMB) extraction unit. The continuous SMB extraction unit has a plurality of n adsorbent beds, and each adsorbent bed has a sequence number j from 1 to n and is functionally disposed in a capture zone, a feed zone, a washing zone, an elution zone, a regeneration zone, and an equilibration zone. Each of the zones is sequentially disposed in parallel from the capture zone being numbered as a first adsorbent bed to the equilibration zone having a last or $n^{th}$ adsorbent bed. Each of the feed zone, the washing zone, the elution zone, the equilibration zone, and the capture zone contains one or more adsorbent beds, and each adsorbent bed has a top and a bottom. Each adsorbent bed contains an adsorbent comprising a quaternary amine cross-linked microcrystalline resin. The process of continuous extraction of heme protein comprises the following steps:
  a) concurrently passing the aqueous protein mixture at SMB feed conditions to the top of the feed zone to load the aqueous protein mixture on the adsorbent in the feed zone and withdrawing a first waste stream comprising water and contaminants from the bottom of the feed zone;
  b) concurrently passing a wash buffer stream to the top of the wash zone to wash the adsorbent in the wash zone to provide a feed purge stream and withdrawing the feed purge stream from the bottom of the wash zone;
  c) concurrently passing at least a portion of the feed purge stream to the top of the capture zone having the first adsorbent bed to capture any unbound protein of interest in the capture zone and provide a first waste stream and withdrawing the first waste stream from the bottom of the capture zone;
  d) concurrently passing an elution buffer to the top of the elution zone and eluting a protein extract product comprising heme protein from the bottom of the elution zone;
  e) concurrently or counter-currently passing a first regeneration buffer comprising a salt and a base to a first portion of the regeneration zone and simultaneously passing a second regeneration buffer comprising an acid to a second portion of the regeneration zone disposed in parallel to the first portion of the regeneration zone and withdrawing a second waste stream from the first and second portions of the regeneration zones;
  f) concurrently passing an equilibration buffer to the top of the equilibration zone having the last adsorbent bed to restore ionic activity to the adsorbent in the equilibration zone and withdrawing a third waste stream from the bottom of the equilibration zone; and, indexing the adsorbent beds wherein the first adsorbent bed in the capture zone is advanced to the feed zone and the last adsorbent bed is advanced to the capture zone to provide a continuous process.

In another embodiment, the invention is a process for the continuous extraction of at least one protein of interest from a crude protein in a continuous simulated moving bed (SMB) extraction zone. The process comprises:
  a) admixing a crude protein comprising the at least one protein of interest, other proteins, and impurities with an equilibration buffer stream comprising a phosphate salt of sodium or potassium and water to provide an SMB feed stream:
  b) continuously passing the SMB feed stream at SMB feed conditions and a plurality of wash streams to the continuous simulated moving bed (SMB) extraction zone, the continuous SMB extraction zone having a plurality of adsorbent beds, one or more of the adsorbent beds being disposed in a loading zone, a washing zone, a elution zone, a regeneration zone, an equilibration zone, and optionally a capture zone or a second washing zone, each of the zones being sequentially disposed in parallel from the loading zone having a first adsorbent bed in a first position to the equilibration zone having a last adsorbent bed in a last position, each of the loading zone, the washing zone, the elution zone, the equilibration zone, and the equilibrium zone containing the one or more adsorbent beds, each of the one or more adsorbent beds having a top and a bottom and each of the one or more adsorbent beds containing an adsorbent selected from the group consisting of a strong anion exchange resin and a quaternary amine cross linked microcrystalline resin, said plurality of wash streams having a pH of from about 7.9 to about 8.2 including a wash buffer stream, an elution buffer stream, a regeneration buffer stream, and the equilibrium buffer stream, said continuous SMB extraction zone comprising:
  i) concurrently passing the SMB feed stream at SMB feed conditions to the top of the loading zone containing a first adsorbent bed to load the SMB feed mixture on the adsorbent in the loading zone and withdrawing a first waste stream comprising water and impurities from the bottom of the loading zone;
  ii) concurrently passing the wash buffer stream comprising phosphate salt of sodium or potassium to the top of the washing zone to wash the adsorbent in the wash zone to provide a wash effluent stream and withdrawing the wash effluent stream from the bottom of the wash zone;
  iii) concurrently passing the elution buffer comprising phosphate salt of sodium or potassium and chloride salt of sodium or potassium to the top of the elution zone and eluting an elution effluent stream comprising the protein of interest from the bottom of the elution zone;
  iv) concurrently or counter-currently passing the regeneration buffer comprising phosphate salt of sodium or potassium and a base to the regeneration zone and withdrawing a second waste stream from the regeneration zone;
  v) concurrently passing the equilibration buffer comprising phosphate salt of sodium or potassium and optionally a chloride salt of sodium or potassium to the top of the equilibration zone comprising the last adsorbent bed to restore ionic activity to the adsorbent in the equilibration zone and withdrawing a third waste stream from the bottom of the equilibration zone; and,
  vi) indexing the adsorbent beds wherein the first adsorbent bed in the loading zone is advanced by one adsorbent bed toward the equilibration zone and the last adsorbent bed in the equilibration zone is repositioned to the first position in the loading zone to provide the continuous SMB process;
c) passing the first waste stream, the second waste stream, the third waste stream, and at least a portion of the wash effluent stream to waste disposal; and,
d) recovering the elution effluent stream as a protein product stream comprising the protein of interest.

In a still further embodiment, the invention is an adsorbent for use in chromatographic separation and extraction of protein. The adsorbent comprises a microcrystalline cellulose which has been cross linked with epichlorohydrin and reacted with 2,3-epoxypropyltrimethyl-ammonium chloride.

BRIEF DESCRIPTION OF THE DRAWINGS

FIG. 1 is a schematic process flow diagram of the simulated moving bed separation process illustrating one embodiment of the invention.

FIG. 7 is an area plot of the composition of the eluate fractions withdrawn from the protein purification process of one embodiment of the invention for purifying RuBisCO on a strong anion exchange resin.

FIG. 15 is gel electrophoresis result of an SDS-PAGE protein analysis using 4-12% Bis-Tris Gel of the elute fractions produced in Example 6.

DETAILED DESCRIPTION OF THE INVENTION

Figure 2A:
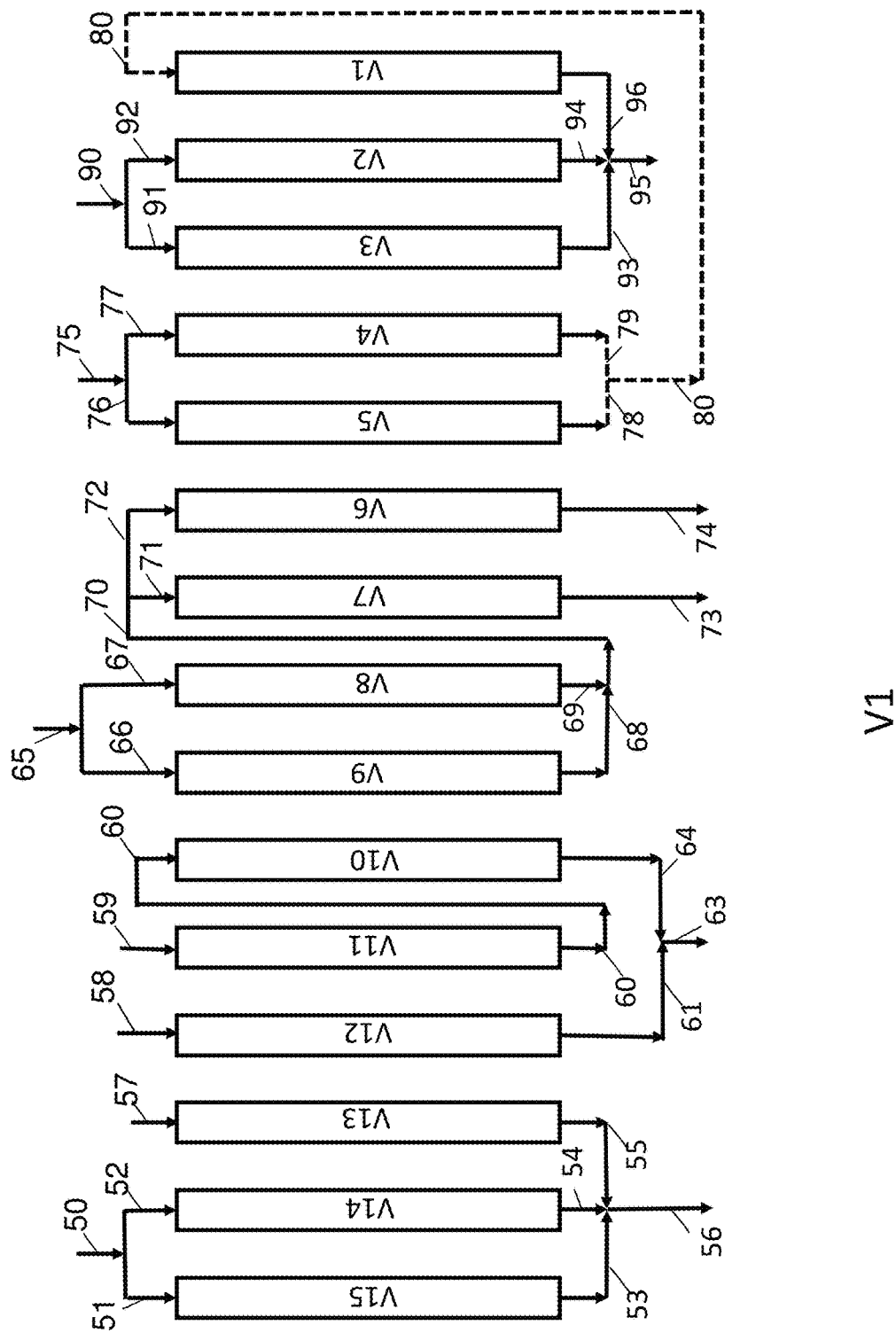
FIG. 2a is a schematic process flow diagram of the simulated moving bed separation process illustrating one embodiment of the invention using 15 adsorbent beds.

Proteins are complex ampholytes that have both positive and negative charges. Ionic interactions are the basis for purification of proteins by ion exchange chromatography. Ion exchange chromatography is one of the most powerful protein purification technique and most frequently used chromatographic technique used for the separation of proteins. The separation is due to competition between proteins with different surface charges for oppositely charged groups on an ion exchange adsorbant. The properties of the ion exchanger will also influence the separation. The structural backbone of the ion exchange resin can be made up of different types of polymer backbones, fixed groups with different chemistries.

Ion exchange chromatography relies on the reversible adsorption-desorption of ions in solution to a charged solid matrix or polymer network. This technique is the most commonly used chromatographic technique for protein separation. A positively charged matrix is called an anion-exchanger because it binds negatively charged ions (anions). A negatively charged matrix is called a cation-exchanger because it binds positively charged ions (cations). The buffer conditions (pH and ionic strength) are adjusted to favor maximum binding of the protein of interest to the ion-exchange column. Contaminating proteins, which bind weakly will pass more rapidly through the column while those bind strongly will elute at higher concentrations of salt compared to the protein of interest. The protein of interest is then eluted using another buffer solution which favors its desorption at a specific salt concentration from the column (e.g., different pH or ionic strength).

Stationary Phase

The stationary phase for use in the continuous simulated moving bed process of the present invention comprises or contains a strong anion exchange resin which has a backbone matrix comprising a cross linked styrene divinyl benzene polymer, a hydroxylated polymethacrylate polymer, or a cross linked microcrystalline cellulose resin. More specifically, Applicant developed a cross linked microcrystalline cellulose resin with quaternary amine which provided a stable and easily regenerated stationary phase for SMB operation. An example of a strong anion exchange resin having a backbone matrix comprising a cross linked styrene divinyl benzene polymer include DIAION HPA25L, a strongly basic anion which represented a strong anion exchange resin with exchange resin (Available from Mitsubishi Chemical Company, Tokyo, Japan). An example of a strong anion exchange resin having a backbone matrix comprising a hydroxylated polymethacrylate polymer is TOYOPEARL GIGACAP Q-650, a high capacity, high resolution, strong anion exchange resin (Available from Tosoh Bioscience LLC, King of Prussia, Pa.). These strong anion or strong basic exchange resins provided a selective adsorption of the protein of interest from a mixture of the protein of interest in dilute aqueous mixtures and in the presence of impurities such as lipids, color impurities. A key property of the adsorbents of the present invention is the ability of the adsorbent to be regenerated within the operation of cycle of the SMB process and restore the adsorbent to its initial adsorption activity. Applicant discovered a novel adsorbent prepared by crosslinking a microcrystalline cellulose with epichlorohydrin and exchanging the cross linked microcrystalline cellulose with a quaternary amine (2,3-epoxypropyltrimethyl-ammonium chloride (glycidyltrimethylammonium chloride) to provide a quaternary amine cross-linked microcrystalline resin having a backbone matrix comprising a cross linked microcrystalline cellulose resin.

Mobile Phase Desorbent

Unlike a traditional SMB process which uses a single mobile phase desorbent to sweep the adsorbent in the adsorbent beds, the present invention employs a series of different desorbent buffer solutions in different portions of the process to facilitate the steps of the SMB process. For example, the SMB process of the present invention comprises a feed step, a wash step, an elution step, a regeneration step, and an equilibration step. All of these steps are carried out in a repeating parallel sequence, in a manner which allows the continuous flow of feed to the SMB process and the continuous production of the protein product. Also produced by the process are a number of waste steams which are aqueous streams and represent spent buffer solutions which may contain salts, unbound/bound proteins or protein fragments, and small molecules. The waste streams generated or withdrawn from the SMB may be neutralized and disposed of in a conventional manner. By way of example for the extraction of heme protein, such as leghemoglobin, from yeast lysate, in the wash step, a wash buffer comprising potassium phosphate, concentration of 2-10 mM and having a pH of about 7.5 to 8.5 and a conductivity of between 0.5 and 2 mS/cm. More preferably, the wash buffer has a potassium phosphate concentration of 3-6 mM. In the elution step, an elution buffer comprising potassium phosphate and sodium chloride and having a pH of 7.5-8.5 and a conductivity of 5-10 mS/cm is employed to elute the protein from the adsorbent and recover the protein product. In the regeneration step, preferably two regeneration buffer solutions are employed to regenerate the adsorbent and reestablish the ionic balance of the adsorbent. A first regeneration buffer comprising sodium hydroxide and sodium chloride is employed to remove tightly bound contaminants from the adsorbent and a second regeneration buffer is employed as an acid wash to restore the activity of the adsorbent. The second regeneration buffer comprises a dilute solution of hydrochloric acid (HCl) or phosphoric acid ($H_3PO_4$). The first regeneration buffer comprises a concentration of sodium hydroxide of about 0.1 N-2 M NaOH and a concentration of sodium chloride of about 0.5-2 M NaCl. The second regeneration buffer has a concentration of hydrochloric acid of about 0.1 N-0.2 N HCl or 0.1 N-0.2 N $H_3PO_4$. In the equilibration step, an equilibration buffer was employed to return the adsorbent to its original ionic strength by contacting the adsorbent with an aqueous solution containing potassium phosphate. It was discovered that to carry out the SMB process wherein the above mentioned major steps of the process could be carried out in essentially equal step times within the SMB cycle, that the equilibration step must be carried out in at least two stages. In the first equilibration stage, a first equilibration buffer comprising potassium phosphate and having a pH of about 7.5 to 8.5 was passed through the adsorbent bed following the regeneration step. The first equilibration buffer had a potassium phosphate concentration of about 50-200 mM potassium phosphate at the required pH. In the second equilibration step the second equilibration buffer was a 2-10 mM solution of potassium phosphate having a pH of between about 7.5 and 8.5.

Feed Preparation

In the present invention, the feed can be a yeast extract such as lysate, or crude protein, admixed with water, such as deionized water or an equilibration buffer to provide an SMB feed mixture. The crude feed mixture may comprise a protein of interest such as the heme protein, leghemoglobin, as well as other proteins, protein fragments, small molecules, and salts. The concentration of total protein in the feed mixture comprise or contain between about 1.5 to about 10 grams of crude protein per liter of feed mixture. It is also important to prevent degradation of the feed by maintaining the temperature of the feed mixture at an SMB feed temperature which is at or below about 4° C. and to maintain a feed pH of between about 7.5 and about 8.5. More preferably the pH of the feed mixture should be maintained at about 8.0.

DETAILED DESCRIPTION OF THE DRAWINGS

With reference to FIG. 1, the following adsorbent bed organization relates to a simulated moving bed (SMB) separation process for the continuous separation of heme proteins from a crude feed mixture comprising yeast and water. As shown in FIG. 1, in a simplified form, the simulated moving bed of the present invention comprises 6 adsorption zones: Capture zone 31, Feed Loading Zone 32, Wash Zone 33, Elution Zone 34, Regeneration Zone A 35 and Regeneration Zone B 36, and Equilibration Zone 37. Each of the 6 adsorption zones may comprise one or more adsorbent columns arranged in parallel, wherein each adsorbent column is filled with or contains and adsorbent consisting of a strong anion exchange resin or a quaternary amine cross-linked microcrystalline resin for the concentration and recovery of heme protein in the crude feed mixture. The crude feed mixture comprises an aqueous solution or suspension of yeast lysate in a feed concentration of from about 1.5 to 10 grams of crude protein, such as lysate, per liter. More preferably, the crude feed mixture comprises a feed concentration of from about 1.5 to 10 grams of crude protein per liter. The crude feed mixture is maintained at an SMB feed temperature at or below about 4° C. and pH adjusted to have a pH of between about 7.5 to about 8.5 and an a feed electrical conductivity, or feed specific conductance, of about 0.5 to about 2.0 mS/cm (milliSiemens/centimeter), and more preferably a feed specific conductance of about 0.8 to about 1.5 mS/cm (milliSiemens/centimeter). In a given SMB cycle, the feed mixture in line 10 is passed to the top of feed loading zone 32 and therein the feed mixture is contacted with the adsorbent at a feed pH of 7.5 to about 8.5 and a feed temperature of less than or equal to about 4° C. The crude feed mixture is passed through the feed loading zone 32 in a concurrent direction; that is, from the top of the feed loading zone to the bottom of the feed loading zone. As the feed mixture in line 10 is loaded on the feed loading zone 32, a first waste stream in line 12 is withdrawn from the feed loading zone 32. The first waste stream in line 12, comprising water and unbound protein may be neutralized and disposed of in any conventional manner. A wash buffer in line 14 is passed to the wash zone 33 in a concurrent direction from the top of the wash zone to the bottom of the wash zone and a second waste stream is withdrawn in line 16. At least a portion of the second waste stream in line 16 is employed to concurrently purge the capture zone 31 to prepare the capture zone 31 for the introduction of the feed mixture and a third waste stream is withdrawn in line 1. An elution buffer in line 18 is concurrently passed to the top of the elution zone 34 and a protein product stream in line 20 is withdrawn from the bottom of the elution zone 34. A first regeneration buffer in line 22 comprising a sodium base and a sodium salt is passed counter currently to the bottom of regeneration zone A 35 to remove any tightly bound contaminants from the adsorbent and simultaneously a second regeneration buffer comprising an acid (such as HCl or $H_3PO_4$) is passed counter-currently to regeneration zone B to acid wash the adsorbent and a fourth waste stream is withdrawn from the tops of regeneration zones A (35) and B (36) in line 24. The fourth waste stream in line 24 may be neutralized and passed to waste disposal in a conventional manner. Regeneration of the regeneration zones 35 and 36 with countercurrent passing of the regeneration buffers assures the removal of impurities which buildup at the top of the adsorbent columns in the regeneration zones during the operation of the SMB process. An equilibration buffer in line 26 is passed concurrently to the top of the equilibration zone 37 to equilibrate the adsorbent and a fifth waste stream is withdrawn in line 28. The fifth waste stream may be passed to neutralization and waste disposal, or alternatively recycled after pH adjustment and filtration to offset the amount of the equilibration buffer in line 26. Each of the above steps takes place during each time period of the SMB cycle. At the end of the period, the cycle is indexed or incremented by shifting the all or a portion of each of the 6 adsorption zones one increment to the left wherein one or more of the adsorption beds in the equilibration zone 37 is moved to the capture zone 31. To accomplish this shift, a rotary valve or a valve switching controller permits the beds to be shifted in function without physically moving the adsorption beds between the zones, or the adsorption zones may be physically rotated about a valve manifold on a carousel which accomplishes the incrementing or shifting of the adsorption beds to the left, or counter to the direction of the mobile phase.

Figure 2:
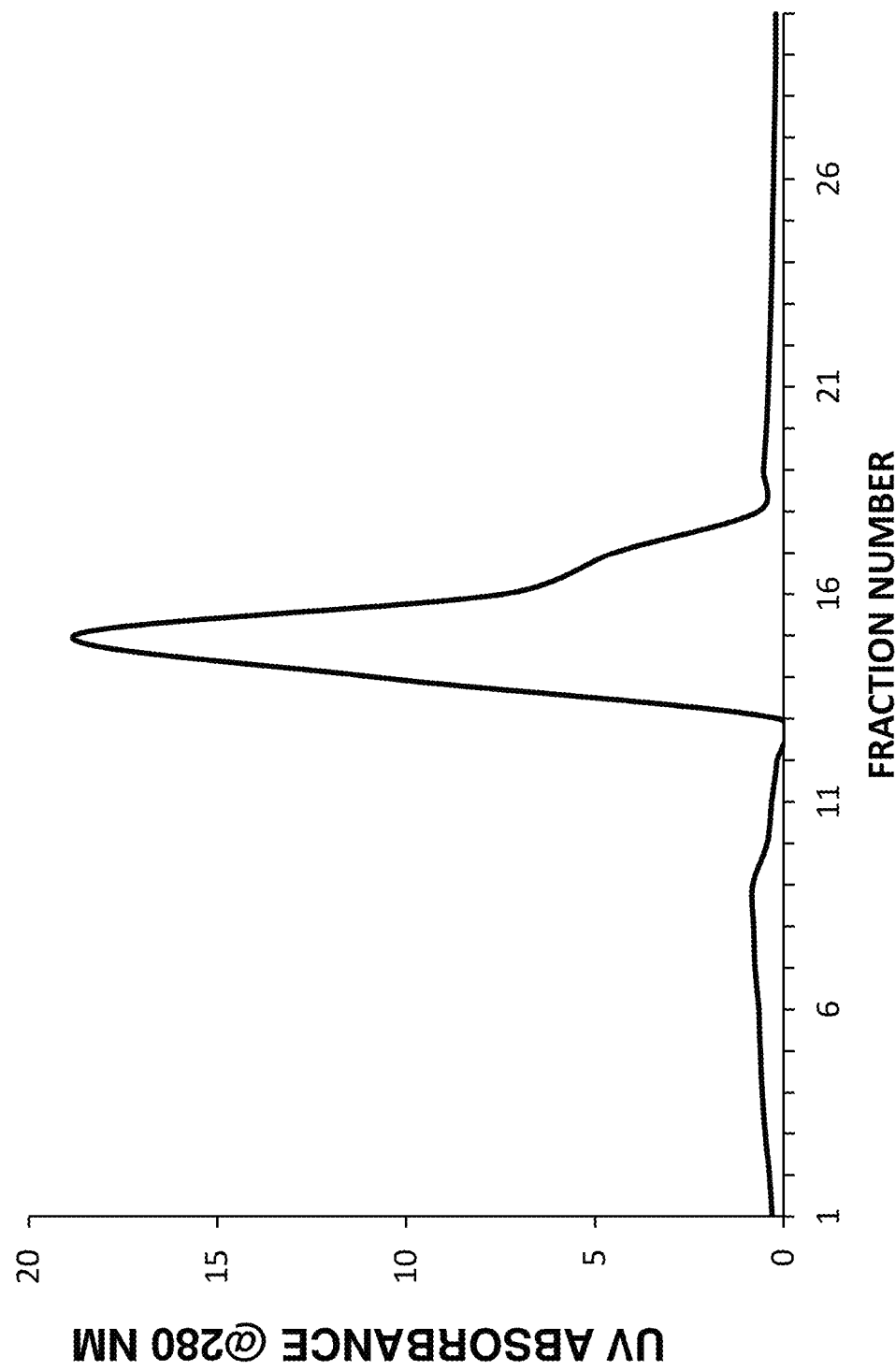
FIG. 2 is a schematic process flow diagram of the simulated moving bed separation process illustrating one embodiment of the invention using 15 adsorbent beds

In another embodiment of the invention is illustrated using 15 adsorption beds in FIG. 2 for simulated moving bed (SMB) separation process for the continuous separation of heme proteins (leghemoglobin) from a feed mixture comprising yeast lysate and water. As shown in FIG. 2, the simulated moving bed of the present invention comprises 15 adsorption beds (V1-V15) disposed in adsorption zones: Capture Zone (V1), Feed Loading Zone (V2-V3), Wash Zone (V4-V5), Elution Zone (V6-V9), First Regeneration Zone A (V10-V11) and Second Regeneration Zone B (V12), and Equilibration Zone (V13-V15). Each adsorbent bed has a top and a bottom. The individual adsorption beds (V1-V15) and are arranged serially from left to right and grouped in the five functionally isolated segments. Each isolated segment comprises at least one or more of the adsorbent beds. In each isolated segment, with the exception of the regeneration zone, an external stream is introduced to the top of a first adsorbent bed in the isolated segment and a waste stream or a product stream is withdrawn from the bottom of the last adsorbent bed in sequence serially, from left to right. In the regeneration zone of the process scheme shown in FIG. 2, the regeneration zone adsorbent beds are processed in a counter current manner, wherein the external streams are introduced at the bottom of the adsorbent bed, and the effluent is withdrawn from the top of the adsorbent bed. Each of the adsorbent beds contains a stationary phase adsorbent which is selective for the adsorption of protein as described hereinabove. According to FIG. 2, a protein feed stream in line 90, such as a crude lysate stream comprising crude lysate and water, is split into a first feed portion in line 92 and a second feed portion in line 91. The first feed portion in line 92 is introduced to the top of adsorbent bed V2 and a first waste effluent in line 94 is withdrawn from adsorbent bed V2. The second feed portion in line 91 is introduced to the top of adsorbent bed V3, operating in parallel to adsorbent bed V2, and a second waste effluent stream is withdrawn in line 93 from the bottom of adsorbent bed V3. A feed buffered wash stream in line 80 is introduced to the top of adsorbent bed V1 to prepare adsorbent bed V1 for processing the feed stream and a third waste effluent stream is withdrawn from adsorbent bed V1 in line 96. The feed buffered stream in line 80 comprises a 2-10 mM sodium phosphate solution and has a pH ranging from 7.5 to 8.5, preferably a pH of 8.0, and a conductivity of from about 0.5-2.0 mS/cm. The first waste effluent stream in line 94, the second waste effluent stream in line 93, and the third waste effluent stream in line 96 are admixed to provide a first waste stream in line 95. The first waste stream is passed to waste disposal. A wash buffer stream in line 75 is split into a wash buffer "A" portion in line 77 and a wash buffer "B" portion in line 76. The wash buffer stream in line 75 comprises a 2-10 mM sodium phosphate solution and has a pH of 7.5 to 8.5 and a conductivity of from about 0.5-2.0 mS/cm. The wash buffer A portion in line 77 is introduced to the top of adsorbent bed V4 and a first spent wash buffer is withdrawn in line 79. The wash buffer B portion in line 76 is introduced to the top of adsorbent bed V5 and a second spent wash buffer is withdrawn in line 78. The first spent wash buffer in line 79 and the second spent wash buffer in line 78 are admixed to form the feed buffered stream in line 80. An elution buffer in line 65 comprises a mixture of a 2-10 mM solution of potassium phosphate and a 25-60 mM solution of sodium chloride and has a pH of from 7.5 to 8.5, preferably a pH of 8.0, and a conductivity of 3-10 mS/cm, and is at room temperature of about 25° C. The elution buffer in line 65 is split into an elution buffer A in line 67 and an elution buffer B in line 68. The elution buffer "A" in line 67 is introduced or passed to the top of adsorbent bed V8 and an intermediate eluate "A" is withdrawn from the bottom of adsorbent bed V8 in line 69. Similarly, elution buffer "B" in line 67 is introduced or passed to the top of adsorbent bed V9 and an intermediate eluate "B" is withdrawn from the bottom of adsorbent bed V9 in line 68. The intermediate eluates A and B are admixed or combined in line 70 as a combined intermediate eluate and again split into a first intermediate eluate in line 72 and a second intermediate eluate in line 71. The first intermediate eluate is passed to the top of adsorbent bed V6 and a first protein product stream is withdrawn in line 74. Similarly, the second intermediate eluate is passed to the top of adsorbent bed V7 and a second protein product stream is withdrawn in line 73. The enriched protein product stream can be characterized as having at least 75 wt % protein purity and having a protein content of ~0.5 g/L. By the term protein purity it is meant that in 100 g of total purified protein, 75 g is the protein of interest. Adsorbent beds V10-V12 comprise the regeneration zone. In the regeneration zone, the regeneration process comprises either concurrently passing (See FIG. 2a), or counter currently passing (See FIG. 2) separate regeneration buffers to separate portions of the regeneration zone. The regeneration zone is divided into a first regeneration zone comprising adsorbent beds V11 and V10, and a second regeneration zone comprising adsorbent bed V12. With reference to a counter current passing of the regeneration buffers through the regeneration zone, in the first regeneration zone, a first regeneration buffer comprising a mixture of a 0.1-2 Normal (N) sodium hydroxide and 0.5-2 Molar (M) solution of sodium chloride in water in line 59 is introduced to the bottom of adsorbent bed V11 and a first regeneration intermediate stream is withdrawn from the top of adsorbent bed V11 in line 60. The first regeneration buffer counter currently flushes the adsorbent beds in the first regeneration zone to remove essentially all of undesired tightly bound proteins and other contaminants, such as lipids, color impurities which have concentrated in layers toward the top of the adsorbent beds V10, V11, and V12 during the SMB process. The first regeneration intermediate stream is passed to the bottom of adsorbent bed V10 and a first regeneration waste stream is withdrawn in line 64. In the second regeneration step, a second regeneration buffer stream in line 58 comprising a 0.1-0.2 N solution of hydrochloric acid is introduced to the bottom of adsorbent bed V12 and a second regeneration waste stream is withdrawn in line 61. The second regeneration buffer counter currently flushes the second regeneration zone of any remaining undesired contaminants and acid washes the adsorbent bed V12 to restore initial activity to the stationary phase adsorbent. The first and second regeneration waste streams in lines 61 and 64 are admixed or combined in line 63 to provide a combined regeneration waste stream. The regeneration waste stream in line 63 is passed to waste disposal. The equilibration zone comprises a first equilibration zone as adsorbent bed V13, and a second equilibration zone as adsorbent beds 14 and 15. A first equilibration buffer in line 57 comprising a solution of 50-200 mM (milliMolar) sodium phosphate and having a pH of about 8 is passed to the top of adsorbent bed 13 and a first equilibration waste stream is withdrawn from the bottom of adsorbent bed V13 on line 55. A second equilibration buffer in line 50 comprising a 4 mM solution of potassium phosphate to provide the final equilibration of the stationary phase adsorbent is split equally into lines 52 and 51 and passed to the top of adsorbent beds V14 and V15, respectively. A second equilibration waste stream in line 54 is withdrawn from adsorbent bed V14, and a third equilibration waste stream in line 53 is withdrawn from adsorbent bed V15. The first and second and third equilibration waste streams are combined or admixed in line 56 to provide a combined equilibration waste stream. It was discovered that by dividing the equilibration step into a first equilibration at high concentration of potassium phosphate (50-200 mM solution) followed by a second or final equilibration step using a lower concentration of potassium phosphate (2-10 mM solution), sufficient equilibration of the stationary phase adsorbent can be carried out within a single SMB cycle.

With reference to FIG. 2a, a further embodiment of the invention is illustrated using 15 adsorption beds for simulated moving bed (SMB) separation process for the continuous separation of proteins from a feed mixture comprising yeast lysate and water as described hereinabove in FIG. 2, except that the regeneration zone is operated in a concurrent mode. The description of FIG. 2a is identical to the description of FIG. 2, with the exception of that operation of the regeneration zone (V10-V12) takes place in a concurrent manner. In the concurrent mode in the regeneration zone of FIG. 2a, the external streams are introduced at the top of the adsorbent beds and the effluent is withdrawn from the bottom of the adsorbent beds (V10-V12) in the regeneration zone. As shown in FIG. 2a, the simulated moving bed of the present invention again comprises 15 adsorption beds (V1-V15) disposed in adsorption zones: Capture Zone (V1), Feed Loading Zone (V2-V3), Wash Zone (V4-V5), Elution Zone (V6-V9), First Regeneration Zone A (10-V11) and Second Regeneration Zone B (V12), and Equilibration Zone (V13-V15). Each adsorbent bed has a top and a bottom. The individual adsorption beds (V1-V15) and are arranged serially from left to right and grouped in the five functionally isolated segments. Each isolated segment comprises at least one or more of the adsorbent beds. In every isolated segment, an external stream is introduced to the top of a first adsorbent bed in the isolated segment and a waste stream or a product stream is withdrawn from the bottom of the last adsorbent bed in sequence serially, from left to right. In the concurrent regeneration zone, the regeneration process comprises concurrently passing separate regeneration buffers to separate portions of the regeneration zone. The regeneration zone is divided into a first regeneration zone comprising adsorbent beds V11 and V10, and a second regeneration zone comprising adsorbent bed V12. With reference to the concurrent passing of the regeneration buffers through the regeneration zone of FIG. 2a, in the first regeneration zone (V10-V11), a first regeneration buffer comprising a mixture of a 0.1-2 M Normal (N) sodium hydroxide and 0.5-2 Molar (M) solution of sodium chloride in water in line 59 is introduced to the top of adsorbent bed V11 and a first regeneration intermediate stream is withdrawn from the bottom of adsorbent bed V11 in line 60. The first regeneration buffer concurrently flushes the adsorbent beds in the first regeneration zone to remove essentially all of undesired tightly bound proteins and other contaminants, such as lipids, color impurities which have concentrated in adsorbent beds V10, and V11 during the SMB process. The first regeneration intermediate stream in line 60 is passed to the top of adsorbent bed V10, and a first regeneration waste stream is withdrawn in line 64. In the second regeneration step, a second regeneration buffer stream in line 58 comprising a 0.1 N solution of hydrochloric acid is introduced to the top of adsorbent bed V12, and a second regeneration waste stream from the bottom of adsorbent bed V12 is withdrawn in line 61. The second regeneration buffer concurrently flushes the second regeneration zone of any remaining undesired contaminants and acid washes the adsorbent bed V12 to restore initial activity to the stationary phase adsorbent. The first and second regeneration waste streams in lines 61 and 64 are admixed or combined in line 63 to provide a combined regeneration waste stream. The regeneration waste stream in line 63 is passed to waste disposal. The remainder of the elements (adsorbent beds and streams) of FIG. 2a are identical to the process scheme described hereinabove in FIG. 2.

Figure 9:
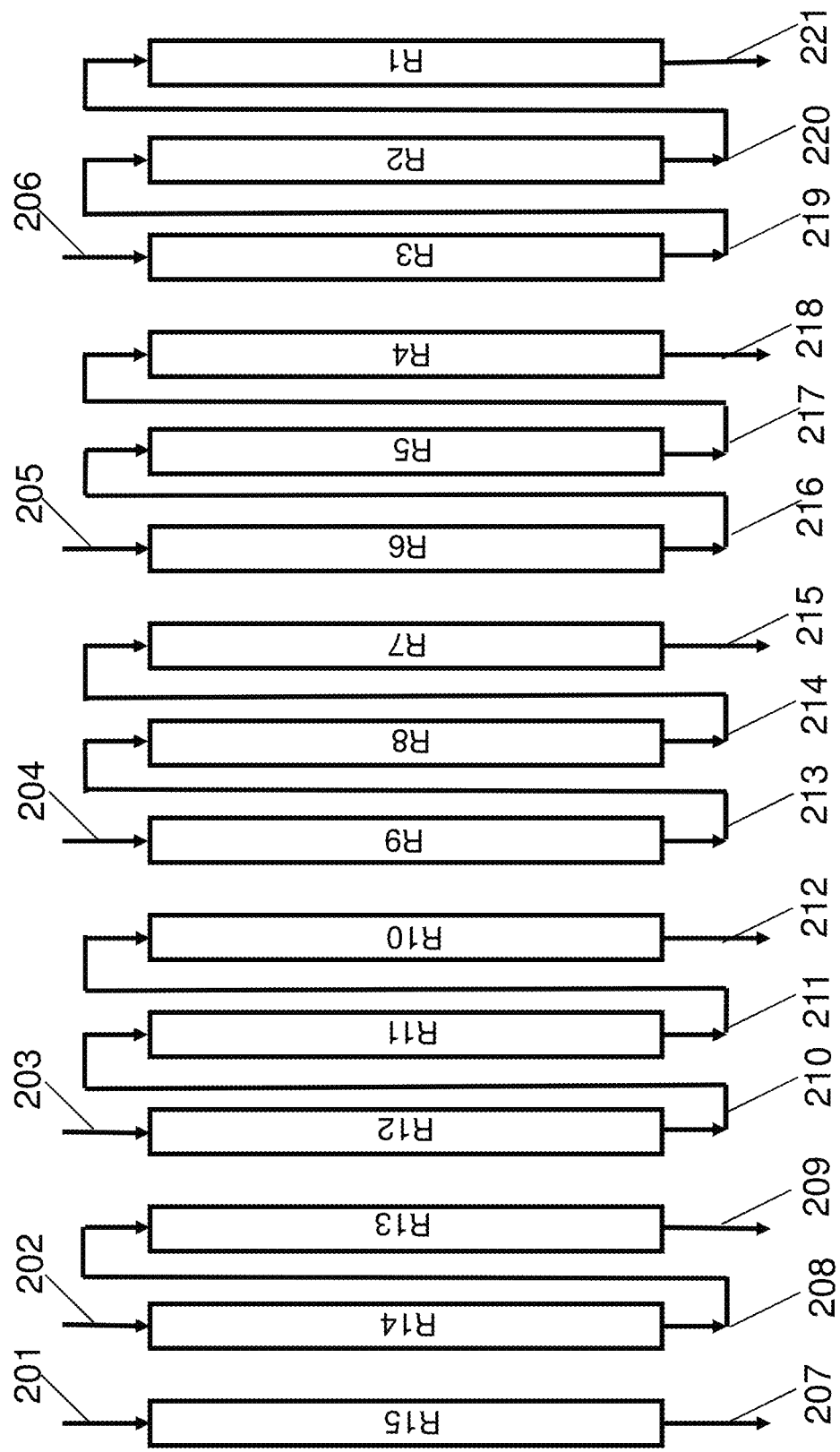
FIG. 9 is a schematic process flow diagram of the simulated moving bed separation process illustrating one embodiment of one embodiment of the invention for extracting RuBisCO.

In a further embodiment of the invention is illustrated using 15 adsorption beds in FIG. 9 for simulated moving bed (SMB) separation process for the continuous separation of a plant protein, RuBisCO protein, from spinach extract. The feed mixture comprising the spinach extract diluted or dispersed in water or an equilibration buffer stream comprising sodium or potassium or sodium phosphate and sodium or potassium chloride in water. As shown in FIG. 9, the simulated moving bed comprises 15 adsorption beds (R1-R15) disposed in adsorption zones: Water Wash Zone (R15), Regeneration Zone (R14-R13), Elution Zone (R12-R10), Washing Zone (R9-R7), Feed Loading Zone (R6-R4), and Equilibration Zone (R3-R1). Each adsorbent bed has a top and a bottom. The individual adsorption beds (R1-R15) and are arranged serially from left to right and grouped in the above six functionally isolated segments. R1 is in a first position and R15 is in the last position. Each isolated segment comprises at least one or more of the adsorbent beds. In each isolated segment an external stream is introduced to the top of a first adsorbent bed in the isolated segment and a waste stream or a product stream is withdrawn from the bottom of the last adsorbent bed (lower number adsorbent bed) in sequence, serially, from left to right. Each of the adsorbent beds contains a stationary phase adsorbent which is selective for the adsorption of protein as described hereinabove. According to FIG. 9, an SMB feed stream comprising the crude protein in line 205 having a spinach concentration of about 0.5-70 g/l is introduced to the top of adsorbent bed R6 in the feed loading zone (R6-R4). The adsorbent beds R6, R5, and R4 are arranged in series, such that the R6 effluent stream withdrawn from the bottom of adsorbent bed R6 in line 216 is passed to the top of adsorbent bed R5, and the R5 effluent stream in line 217 is passed to the top of adsorbent bed R4. In the feed loading zone the protein of interest is disposed on the stationary phase adsorbent in adsorbent beds R6, R5, and R4 and a first waste stream is withdrawn from adsorbent bed R4 in line 218 and passed to neutralization and waste disposal. A wash buffer stream in line 204 comprising sodium or potassium phosphate and sodium or potassium chloride is passed to the top of adsorbent bed R9 in a washing zone (R9-R7) to wash impurities and other proteins from the adsorbent in the washing zone and provide a second waste stream in line 215. The wash buffer stream comprises a wash buffer concentration of from about 2 mM to about 100 mM of phosphate salt of sodium or potassium, and the wash buffer stream has a pH of about 7.5 to 8.5 and a conductivity of between 0.5 and 25 mS/cm. The adsorbent beds R9, R8, and R7 are arranged in series, such that the R9 effluent stream withdrawn from the bottom of adsorbent bed R9 in line 213 is passed to the top of adsorbent bed R8, and the R8 effluent stream in line 214 is passed to the top of adsorbent bed R7. An elution buffer stream in line 203 comprising sodium or potassium phosphate and sodium or potassium chloride and having a concentration of 2 mM to about 100 mM of phosphate salt of sodium or potassium, and from about 0.02 M to about 0.5 M of sodium or potassium chloride is passed to the top of adsorbent bed R12 in an elution zone (R12-R10) to selectively desorb and recover the RuBisCO protein from the adsorbent in the elution zone and provide a product stream in line 212. The adsorbent beds R12, R11, and R10 are arranged in series, such that the R12 effluent stream withdrawn from the bottom of adsorbent bed R12 in line 210 is passed to the top of adsorbent bed R11, and the R11 effluent stream in line 211 is passed to the top of adsorbent bed R10. A regeneration buffer stream in line 202 comprising sodium or potassium hydroxide or a suitable base and sodium or potassium chloride is passed to the top of adsorbent bed R14 in a regeneration zone (R14-R13) to regenerate the adsorbent in the regeneration zone and provide a third waste stream in line 209. The adsorbent beds R14 and R13 are arranged in series, such that the R14 effluent stream withdrawn from the bottom of adsorbent bed R12 in line 208 is passed to the top of adsorbent bed R13. A water stream in line 201 is passed to the top of adsorbent bed R15 and a fourth waste stream is withdrawn from the bottom of adsorbent bed R15. An equilibration buffer stream in line 206 having a concentration of 40 to 100 mM of sodium or potassium phosphate and 0.1 M NaCl is passed to the top of adsorbent bed R3 in the equilibration zone (R3-R1) to reionize and restore the adsorbent in the equilibration zone and provide a fourth waste stream in line 221. The fourth waste stream in line 221 may be neutralized and passed to waste disposal in a conventional manner. The adsorbent beds R3, R2, and R1 are arranged in series, such that the R3 effluent stream withdrawn from the bottom of adsorbent bed R2 in line 219 is passed to the top of adsorbent bed R2, and the R2 effluent stream in line 220 is passed to the top of adsorbent bed R1. The water wash stream removes or flushes any residual salts from the adsorbent in adsorbent bed R15 to prevent any buildup of salts in the system prior to the next feed loading cycle. At the completion of the cycle, the adsorbent beds are indexed by one adsorbent bed to the left, such that the last bed in the series R15 is moved to the first position and R14 is moved to the water wash zone, or the last position. Using the SMB process with an adsorbent such as the strong basic exchange resin, such as TOYOPEARL GIGACAP Q-650, the RuBisCO protein extraction yield was about 72 percent on a weight basis based on the amount of RuBisCO protein in the feed, and the recovered RuBisCO protein purity was about 85 wt %.

Figure 10:
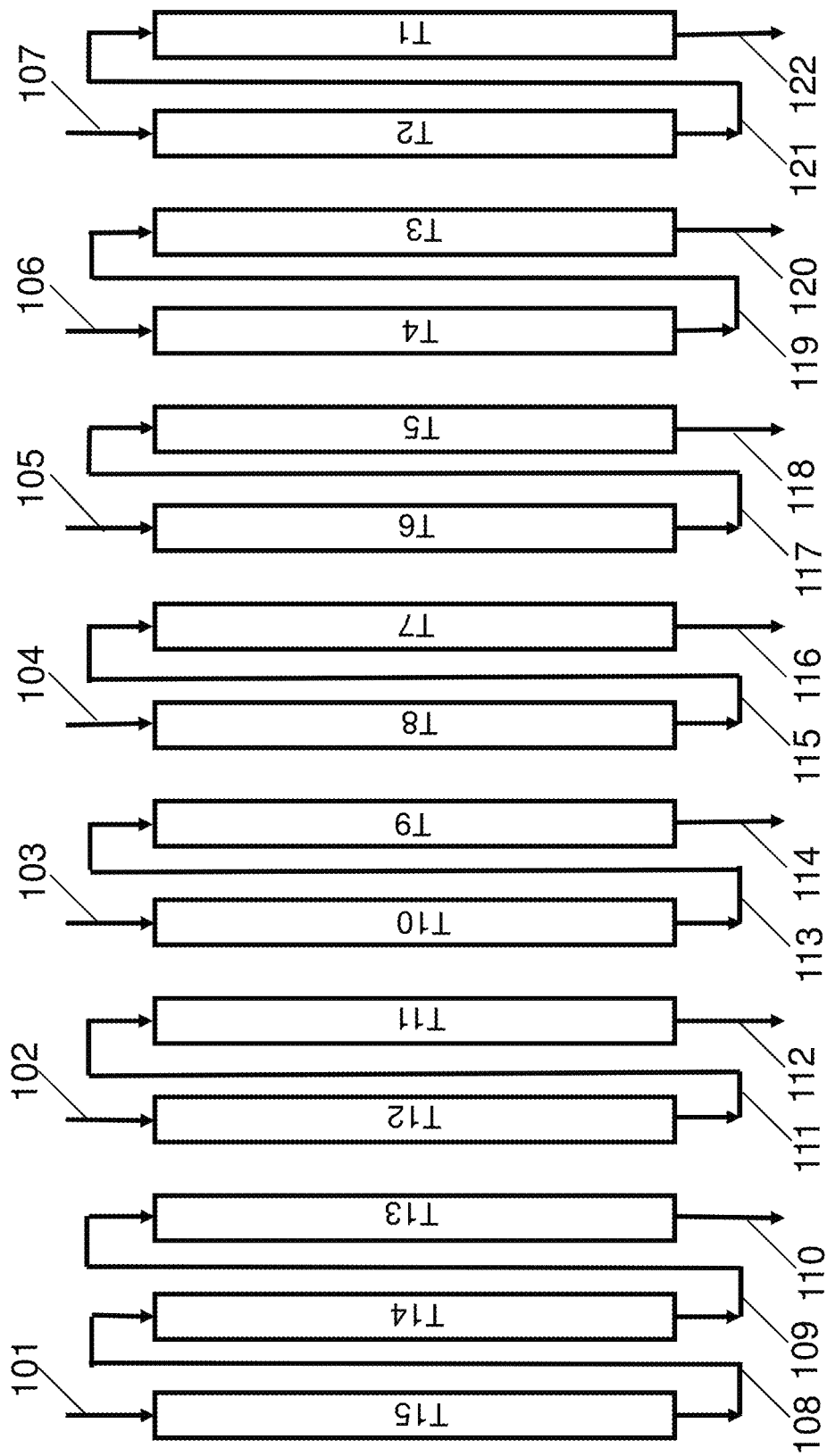
FIG. 10 is a schematic process flow diagram of the simulated moving bed separation process illustrating one embodiment of the invention for extracting pea proteins.

In a still further embodiment of the invention is illustrated using 15 adsorption beds in FIG. 10 for simulated moving bed (SMB) separation process for the continuous separation or extraction of multiple plant proteins, such as multiple proteins in pea protein, from pea flour. The crude feed mixture comprising the pea flour is diluted or dispersed in water or an equilibration buffer stream comprising sodium or potassium or sodium phosphate and sodium or potassium chloride in water. As shown in FIG. 10, the simulated moving bed comprises 15 adsorption beds (T1-T15) disposed in adsorption zones: Regeneration Zone (T15-T13), Elution Zone 3 (T12-T11), Elution Zone 2 (T10-T9), Elution Zone 1 (T8-T7), Washing Zone (T6-T5), Feed Loading Zone (T4-T3), and Equilibration Zone (T2-T1). Each adsorbent bed has a top and a bottom. The individual adsorption beds (T1-T15) and are arranged serially from left to right, and grouped in the above six functionally isolated segments. T1 is in a first position and T15 is in the last position. Each isolated segment comprises at least one or more of the adsorbent beds. In each isolated segment an external stream is introduced to the top of a first adsorbent bed in the isolated segment and a waste stream or a product stream is withdrawn from the bottom of the last adsorbent bed (lower number adsorbent bed) in sequence, serially, from left to right. Each of the adsorbent beds contains a stationary phase adsorbent which is selective for the adsorption of protein of interest as described hereinabove. According to FIG. 10, an SMB feed stream comprising the crude protein in line 106 having a pea flour concentration of about 1 wt % is introduced to the top of adsorbent bed T4 in the feed loading zone (T4-T3). The adsorbent beds T4 and T3 are arranged in series, such that the T4 effluent stream withdrawn from the bottom of adsorbent bed T4 in line 119 is passed to the top of adsorbent bed T3. In the feed loading zone, the proteins of interest are disposed on the stationary phase adsorbent in adsorbent beds T4 and T3, and a first waste stream is withdrawn from adsorbent bed T3 in line 120 and passed to neutralization and waste disposal. A wash buffer stream in line 105 comprising sodium or potassium phosphate and sodium or potassium chloride is passed to the top of adsorbent bed T6 in a washing zone (T6-T5) to wash impurities and other proteins from the adsorbent in the washing zone and provide a second waste stream in line 118. The adsorbent beds T6 and T5 are arranged in series, such that the T6 effluent stream withdrawn from the bottom of adsorbent bed T6 in line 117 is passed to the top of adsorbent bed T5. A first elution buffer stream in line 104 comprising sodium or potassium chloride is passed to the top of adsorbent bed T8 in a first elution zone (T8-T7) to selectively desorb and recover a first group (Group A) of pea proteins of interest from the adsorbent in the first elution zone (T8-T7) and provide a first product stream in line 116. The adsorbent beds T8 and T7 are arranged in series, such that the T8 effluent stream withdrawn from the bottom of adsorbent bed T8 in line 115 is passed to the top of adsorbent bed T7. A second elution buffer stream in line 103 comprising sodium or potassium chloride is passed to the top of adsorbent bed T10 in a first elution zone (T10-T9) to selectively desorb and recover a second group (Group B) of pea proteins of interest from the adsorbent in the first elution zone (T10-T9) and provide a second product stream in line 114. The adsorbent beds T10 and T9 are arranged in series, such that the T10 effluent stream withdrawn from the bottom of adsorbent bed T10 in line 113 is passed to the top of adsorbent bed T9. A third elution buffer stream in line 102 comprising sodium or potassium chloride is passed to the top of adsorbent bed T12 in a first elution zone (T12-T11) to selectively desorb and recover a first group (Group C) of pea proteins of interest from the adsorbent in the third elution zone (T12-T11) and provide a first product stream in line 112. The adsorbent beds T12 and T11 are arranged in series, such that the T12 effluent stream withdrawn from the bottom of adsorbent bed T12 in line 111 is passed to the top of adsorbent bed T11. A regeneration buffer stream in line 101 comprising sodium or potassium chloride sodium and optionally potassium hydroxide or a suitable base is passed to the top of adsorbent bed T15 in a regeneration zone (T15-T13) to regenerate the adsorbent in the regeneration zone and provide a third waste stream in line 110. The adsorbent beds T15, T14 and T13 are arranged in series, such that the T15 effluent stream withdrawn from the bottom of adsorbent bed T15 in line 108 is passed to the top of adsorbent bed T14, the T14 effluent stream withdrawn from the bottom of adsorbent bed T14 in line 109 is passed to the top of adsorbent bed T13. An equilibration buffer stream in line 107 is passed to the top of adsorbent bed T2 in the equilibration zone (T2-T1). The adsorbent beds T1 and T2 are arranged in series, such that the T1 effluent stream withdrawn from the bottom of adsorbent bed T1 in line 121 is passed to the top of adsorbent bed T1. A fifth waste stream is withdrawn from adsorbent bed T1 in line 122 and passed to neutralization and disposal. At the completion of the cycle, the adsorbent beds are indexed by one adsorbent bed to the left, such that the last bed in the series T15 is moved to the first position, and T14 is moved one position to the left, or the last position. Using the SMB process with an adsorbent such as the strong anion or strong basic exchange resin, such as TOYOPEARL GIGACAP Q-650, having a hydroxylated polymethacrylate polymer matrix.

A commercial embodiment of the SMB system of the current invention will arranged for maximum selectivity. The simulated moving bed operation is achieved by use of a plurality of adsorbent beds connected in series and a complex valve system, whereby the complex valve system facilitates switching at regular intervals the feed entry in one direction, the mobile phase desorbent entry in the opposite direction, while changing the eluted product and waste stream takeoff positions as well. The SMB system is a continuous process. Feed enters and the elute product(s) and waste streams are withdrawn continuously at substantially constant compositions. The overall operation is equivalent in performance to an operation wherein the fluid and solid are contacted in a continuous countercurrent manner, without the actual movement of the solid, or stationary phase adsorbent. In a commercial implementation of the present invention, the number of actual adsorbent beds in a particular zone of the SMB is a matter of economic choice and valve size limitations.

The following examples are provided to illustrate the present invention. These examples are shown for illustrative purposes, and any invention embodied therein should not be limited thereto.

EXAMPLES

Example 1—Quaternary Amine Cross-linked Microcrystalline Resin

Part A: Cross-Linking of Microcrystalline Cellulose

The stationary phase adsorbent of the present invention is a quaternary amine cross-linked microcrystalline resin. The quaternary amine cross-linked microcrystalline resin was prepared in the following manner. A 17.53 g of a general purpose emulsifier, RHODAFAC PE-510, a polyoxyethylenenonyl-phenyl ether phosphate (Available from Solvay Chemicals, Houston, Tex.) was weighed in a 500 ml conical flask. A 400 ml portion of cyclohexane was added to the conical flask, stirred for 30 minutes, and allowed to rest over night at a room temperature of about 25° C. A 65 g portion of AVICEL PH-200, a microcrystalline cellulose, (Available from FMC Corporation, Philadelphia, Pa.) having a particle size ranging from about 150 to about 250 microns, an average particle size of 180 um, a loose bulk density of 0.29-0.39 g/cc, and a moisture content of 2.0 to 5.0 wt % was added to a two liter multi-neck reaction flask: a Morton Style round bottom flask, equipped with overhead stirrer, reflux condenser, thermocouple, and an addition funnel. The reaction flask was placed in a heating mantle. A 52 ml portion of a solution of 45% sodium hydroxide and 250 ml of water was added to the reaction flask. The reaction mixture was vigorously stirred (370-380 RPM) for 60 minutes while heating the reaction flask to maintain a reaction temperature of 55° C. The heating was stopped, the emulsifier/cyclohexane mixture in the conical flask was added to the reaction mixture in the reaction flask. The reaction mixture was again stirred vigorously at a stirrer speed of about 420 rpm for an additional 60 minutes while heating the reaction mixture to maintain a reaction temperature of 55° C. A 75 ml first addition of epichlorohydrin was added to the reaction flask in a drop wise manner using the addition funnel over a period of 20 minutes while stirring at 400 RPM and maintaining the reaction flask at a reaction temperature of 55° C. It was observed at one point during the drop wise addition of the first portion of epichlorohydrin that there was an exothermic reaction and a brief temperature excursion to about 59.1° C. Following the addition of the first portion of epichlorohydrin, the reaction mixture was again vigorously stirred at about 405 RPM, (revolutions per minute) for another 60 minutes while maintaining the reaction mixture at about 55° C. At the end of this 60 minute period, a 45 ml (milliliter) portion of a solution of 45 mol % sodium hydroxide and 21 ml of water were added to the reaction flask while stirring and maintaining the reaction flask at 55° C. A second epichlorohydrin addition of 45 ml of epichlorohydrin was added to the reaction flask in a drop wise manner using the addition funnel over a period of 10 minutes while stirring the reaction mixture at a rate of 405 RPM and maintaining the reaction flask at a reaction temperature of 55° C. Again, another temperature excursion occurred briefly reaching 62.5° C. After complete addition of epichlorohydrin, the reaction mixture was stirred at 405 RPM while heating at 55° C. for an additional 60 minutes. The heating of the reaction flask was stopped and the stirring at the rate of 405 RPM was continued for 2 hours. The reaction mixture was then transferred to a 5 liter beaker containing 4 liters of a 1 mol % solution of sodium chloride in deionized water and allowed to rest for 30 minutes to permit the resulting gel to separate from a supernatant, having a cloudy appearance. The supernatant was separated from the gel by being decanted off and discarded. The 4 liters of a 1 mol % solution of sodium chloride in deionized water was admixed with the gel to wash the gel and the mixture of the sodium chloride and gel mixture was allowed to settle for 30 minutes to permit the gel to settle out from the supernatant. The supernatant was again decanted off and discarded. This washing of the gel with the 1 mol % sodium chloride solution 4 more times to provide the washed cross-linked microcellulose gel. The washed cross-linked microcellulose gel was transferred to a Buchner funnel using SHARK SKIN filter paper, a creped, medium-to-slow, wet strength filter paper, having a 12 micron pore size and a diameter of 270 mm (Available from GE Healthcare Life Sciences, Marlborough, Mass.) and washed with 2 liters of 1 mol % sodium chloride aqueous solution. The resulting cross-linked microcellulose gel was stored in an aqueous solution of 1 mol % sodium chloride.

Part B: Reaction of Cross-linked Microcellulose with Quaternary Amine

QUAB 151 (Available from SKW QUAB Chemicals, Inc. Saddle Brook, N.J.) is the an aqueous solution of the active substance 2,3-epoxypropyltrimethyl-ammonium chloride (glycidyltrimethylammonium chloride). The reaction of cross-linked microcellulose gel with the quaternary amine, QUAB 151 was carried out in a second 500 ml reaction flask. A 75 g portion of suction dried cross-linked microcellulosegel prepared in Part A of Example 1 was added to 50 ml of 0.6 N NaOH solution containing sodium borohydride (2 mg/ml) in the second 500 ml reaction flask and stirred. 50 ml of the QUAB 151 was added to the second 500 ml reaction flask and stirred for 20 hours at room temperature (about 25° C.). The resulting reaction mixture was filtered in a Buchner funnel using a SHARK SKIN filter paper, a creped, medium to slow, wet strength filter paper, having a 12 micron pore size and a diameter of 110 mm (Available from GE Healthcare Life Sciences, Marlborough, Mass.) and washed with 3 liters of 1 mol % sodium chloride aqueous solution. The resulting filter cake, or quaternary amine cross-linked microcellulose resin was suction dried and stored at a storage temperature of 4° C.

Example 2—Recombinant Yeast Heme Protein Purification Using Quaternary Amine Cross-linked Microcellulose Resin Approximately 5 gm (5 ml) sample of the adsorbent, the quaternary amine cross-linked microcelluloseresin prepared in Example 1, was packed in a plastic column having an inside diameter of 12 mm and a length of 45 mm. The quaternary amine cross-linked microcellulose resin was first equilibrated by passing 5 column volumes of an equilibration buffer 1 comprising a potassium phosphate solution having a potassium phosphate concentration of 50 mM (millimolar) sodium phosphate, and having a pH 8.0. The equilibration buffer was passed concurrently to the top of the glass column at a rate of 5 ml/min. The resin was then equilibrated by passing 20 column volumes of an equilibration buffer 2 comprising a potassium phosphate solution having a potassium phosphate concentration of 4 mM potassium phosphate, and having a pH 8.0. The effluent from the bottom of the column during the equilibration step was passed to waste disposal. Following equilibration, a feed comprising yeast lysate was loaded on the adsorbent in a feed loading step. A 38 mg sample of yeast lysate which had been stored at −20° C., was thawed at room temperature and diluted with equilibration buffer to adjust the total protein concentration to ~2 mg/ml at 4° C. to provide a feed mixture, and the pH of the feed mixture was adjusted to a pH of 8 with 1 N NaOH on ice, and the conductivity of the feed mixture was about 800 µS. The feed mixture had protein concentration of 2.18 mg/ml which was determined by Pierce 660 nm protein assay. The Pierce 660 nm Protein Assay (Available from Thermo Fischer Scientific, Pittsburgh, Pa.) uses a proprietary dye-metal complex which binds to protein in acidic conditions, causing a shift in the dye's absorption maximum, which is measured at 660 nm. A 17.5 ml portion of the feed mixture was passed to the top of the column at a feed rate of about 0.5 ml/min and the resulting elute was collected 5 ml fractions. The column was then washed with 5 column volumes of a wash buffer comprising an aqueous solution having a potassium phosphate concentration of 4 mM sodium phosphate, and a pH 8.0. The wash buffer was passed to the top of the column at a wash rate of about 0.5 ml/min and the resulting wash effluent was collected in 5 ml fractions. In an elution step, the heme protein was then eluted by passing an elution buffer comprising potassium phosphate and sodium chloride to the top of the column and collecting the eluted heme protein product. The elution buffer comprised a potassium phosphate concentration of 4 mM, and a concentration of sodium chloride of 25 mM sodium chloride and had a pH of 8.0. The elution buffer was passed to the top of the column at an elution rate of 0.5 ml/min (See FIG. 3), and the extracted heme protein product was collected from the bottom of the column. The column was then washed with 5 column volumes of 1 M NaCl solution at a rate of 2 ml/min to elute the other proteins. Protein concentration was again determined by using Pierce 660 nm protein assay. Purity was determined by analyzing the collected product fractions on 4-12% Bis-Tris SDS-PAGE followed by densitometry using Bio-Rad's EZ Imager (See FIG. 4). NuPAGE Bis-Tris gels (Available from Thermo Fischer Scientific, Pittsburgh, Pa.) are precast polyacrylamide gels designed to provide separation of small to medium-sized proteins during gel electrophoresis. Bio-Rad's EZ IMAGER is an automated gel imaging instrument (Available from Bio-Rad, Hercules, Calif.). The adsorbent was regenerated in a regeneration step by washing the column with 10 column volumes of 0.1 M NaOH+1 M NaCl followed by washing the column with 5 column volumes of 0.1 N phosphoric acid. The column was then equilibrated in an equilibration step bypassing 5 column volumes at a rate of 5 ml/min of an equilibration buffer 1 comprising 50 mM potassium phosphate, and having a pH of 8.0. The resin was then equilibrated by passing 20 column volumes of an equilibration buffer 2 comprising a potassium phosphate solution having a potassium phosphate concentration of 4 mM potassium phosphate, and having a pH 8.0. The protein of interest was leghemoglobin protein, and the lysate was determined to contain about 25% percent leghemoglobin protein by weight. The leghemoglobin protein content of the lysate was determined by densitometry to contain 9.53 mg of the approximately 38 mg loaded. The leghemoglobin protein found in the protein product elute fractions (shown in FIG. 4 as Lanes 5-9) was determined to be 11.16 mg. Thus, the heme protein extraction yield was about 97% on a weight basis compared to the amount of heme protein in the feed, and the heme protein purity was about 83%, determined by densitometry.

Figure 3:
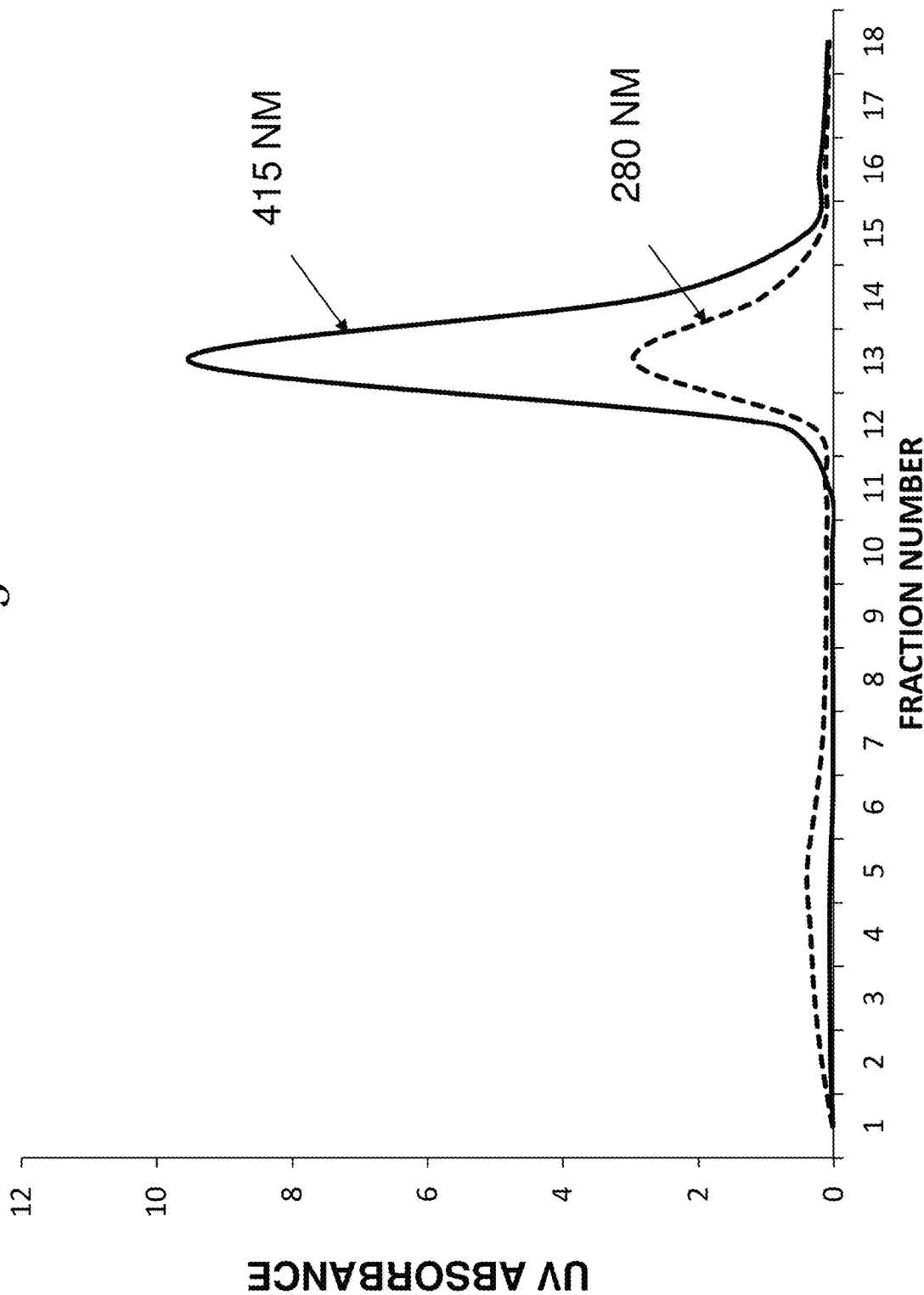
FIG. 3 is an area plot of the composition of the eluate fractions withdrawn from the protein purification process of one embodiment of the invention for heme protein using a cross linked microcellulose adsorbent.
Figure 4:
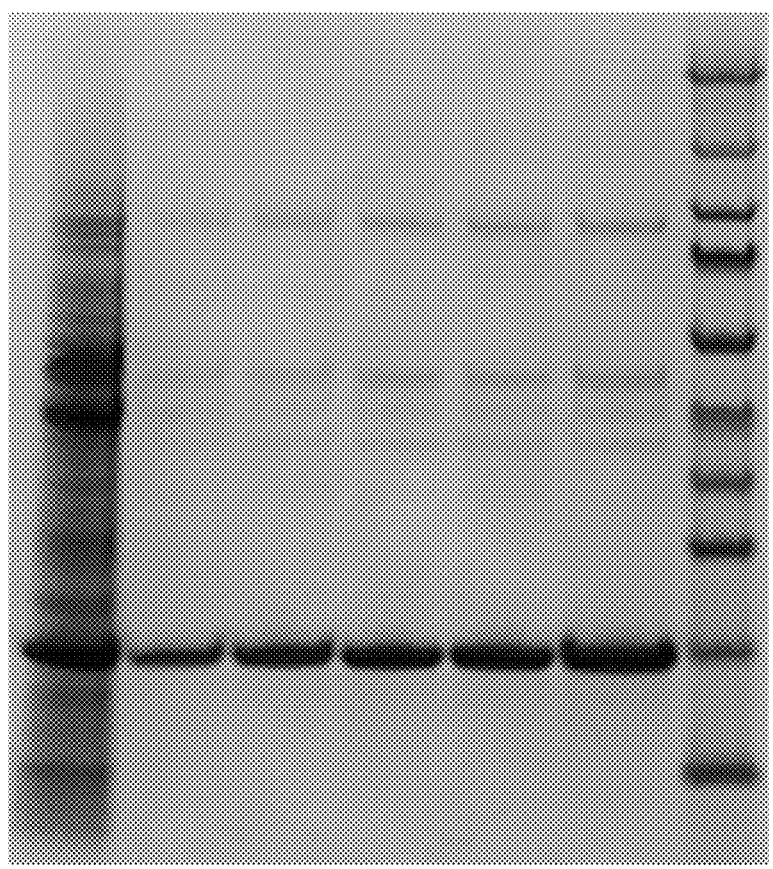
FIG. 4 is a gel electrophoresis result of an SDS-PAGE protein analysis using 4-12% Bis-Tris Gel of the elute fractions produced for heme protein using a cross linked microcellulose adsorbent by one embodiment of the invention.

The analytical results for the extraction of heme protein from the lysate of Example 2 were depicted in graphical form in FIG. 3 and FIG. 4.

FIG. 3 shows the optical density area plot of the protein concentration of the numbered elute fractions withdrawn from the column in Example 2.

FIG. 4 is gel electrophoresis result of an SDS-PAGE protein analysis using 4-12% Bis-Tris Gel of the elute fractions produced in Example 2. FIG. 4 shows the collected elute fractions eluted from the column of Example 2 containing the quaternary amine cross-linked microcellulose resin on 4-12% Bis-Tris SDS-PAGE imager at various points in the SMB process. The results are shown in lanes which are numbered along the x-axis. Lane 1: Feed load, 14 ug (micrograms); Lane 2: Elution pool, 1.08 ug; Lane 3: Elution pool, 1.62 ug; Lane 4: Elution pool, 2.16 ug; Lanes 5: Elution pool, 2.7 ug; Lane 6: 3.1 ug, Lane 7: Molecular weight marker proteins.

Example 3—Heme Protein Purification Using Chromatography with Strong Anion Exchange Resin in a Single Column Separation Example 3 evaluated DIAION HPA25L a strongly basic anion exchange resin having a backbone matrix of styrene divinyl benzene polymer (Available from Mitsubishi Chemical Company, Tokyo, Japan) for use in a single column separation process to determine the ability of the HPA25L resin to provide the required degree of separation and also be regenerable during an SMB cycle.

A. Resin Preparation:

Accordingly, a resin volume of about 5 ml of DIAION HPA25L resin was washed in a resin wash step to remove impurities and any fines. The resin wash step consisted of soaking the volume of the resin in two times the volume (about 10 ml) of resin in a 1:1 (v/v) mixture of 1 M NaOH: methanol for 2 hours at room temperature and at atmospheric pressure. At the end of 2 hours, the supernatant was decanted and the remaining resin solids were washed again with in two times the volume of resin in a 1:1 (v/v) mixture of 1 M NaOH: methanol for 2 hours at room temperature and at atmospheric pressure. After decanting the supernatant, the resin was washed three times with water by soaking the volume of resin in twice the volume of water and allowing the resin/water mixture to stand for about 30 minutes, before decanting the water. The resin was then washed 3 times with a 2 N HCl solution by soaking the resin in twice the volume of HCl solution and allowing the resin/HCl solution to stand for 30 minutes and then decanting the HCl solution. The washed resin was packed in a high-modulus polyethylene, (HMPE) column (having a diameter of about 12 mm and a length of about 45 mm) and washed with water until the eluate had a pH of about 4. The resin was then washed with 3 column volumes of 20 vl % ethanol and stored at room temperature.

B. Heme (Leghemoglobin) Protein Purification:

The washed resin (approximately 5 g or 5 ml) in the packed HMPE column, prepared hereinabove in Example 3—Part A, was washed with 5 column volumes of 50 mM (milliMolar) sodium phosphate solution having a pH of 8.0 at a rate of 0.5 ml/min. The resin was equilibrated by passing 10 column volumes of a 5 mM sodium phosphate solution having a pH of 8.0 at 0.5 ml/min. A 34.125 mg portion of yeast lysate which had been stored at a storage temperature of −20° C. was diluted a 5 mM sodium phosphate solution having a pH of 8.0 to provide about a 17.5 ml feed mixture which was maintained on ice at a temperature of about 4° C. The feed mixture had a conductivity of about 1.0 mS (milliSiemans). In a loading step, the 17.5 ml of the feed mixture was passed through the column or loaded on the resin at a rate of about 5 ml/min and the eluate was collected in 5 ml fractions. In a washing step, the column was washed with about 5 column volumes of a 5 mM solution of sodium phosphate having a pH of 8.0 at a rate of 0.5 ml/min and the resulting wash eluate was collected in 5 ml fractions. The heme protein remaining on the resin after the wash step was eluted in an elution step by flushing the column with 5 column volumes of an elution buffer of 5 mM sodium phosphate and 50 mM sodium chloride and having a pH of 8.0. The protein eluate was collected at 5 ml fractions and stored on ice at a temperature of 4° C. The remaining proteins on the resin were eluted by flushing the column with a 1 M solution of sodium chloride. The protein concentration in the collected fractions was determined by Pierce 660 nm protein assay. The Pierce 660 nm Protein Assay (Available from Thermo Fischer Scientific, Pittsburgh, Pa.) uses a proprietary dye-metal complex which binds to protein in acidic conditions, causing a shift in the dye's absorption maximum, which is measured at 660 nm. Purity of the protein was determined by analyzing the collected product fractions on 4-12% Bis-Tris SDS-PAGE followed by densitometry using Bio-Rad's EZ Imager (See FIG. 6). NuPAGE Bis-Tris gels (Available from Thermo Fischer Scientific, Pittsburgh, Pa.) are precast polyacrylamide gels designed to provide separation of small to medium-sized proteins during gel electrophoresis. Bio-Rad's EZ IMAGER is an automated gel imaging instrument (Available from Bio-Rad, Hercules, Calif.). The heme protein content of the lysate was determined by densitometry to contain 7.47 mg of the approximately 34.125 mg loaded. The heme protein found in the protein product elute fractions (shown in FIG. 6 as Lanes 7-10) was determined to be 5.9 mg. Thus, using the strong basic resin DIAION HPA25L the heme protein extraction yield was about 79% on a weight basis compared to the amount of heme protein in the feed, and the heme protein purity was about 79%, determined by densitometry.

Figure 5:
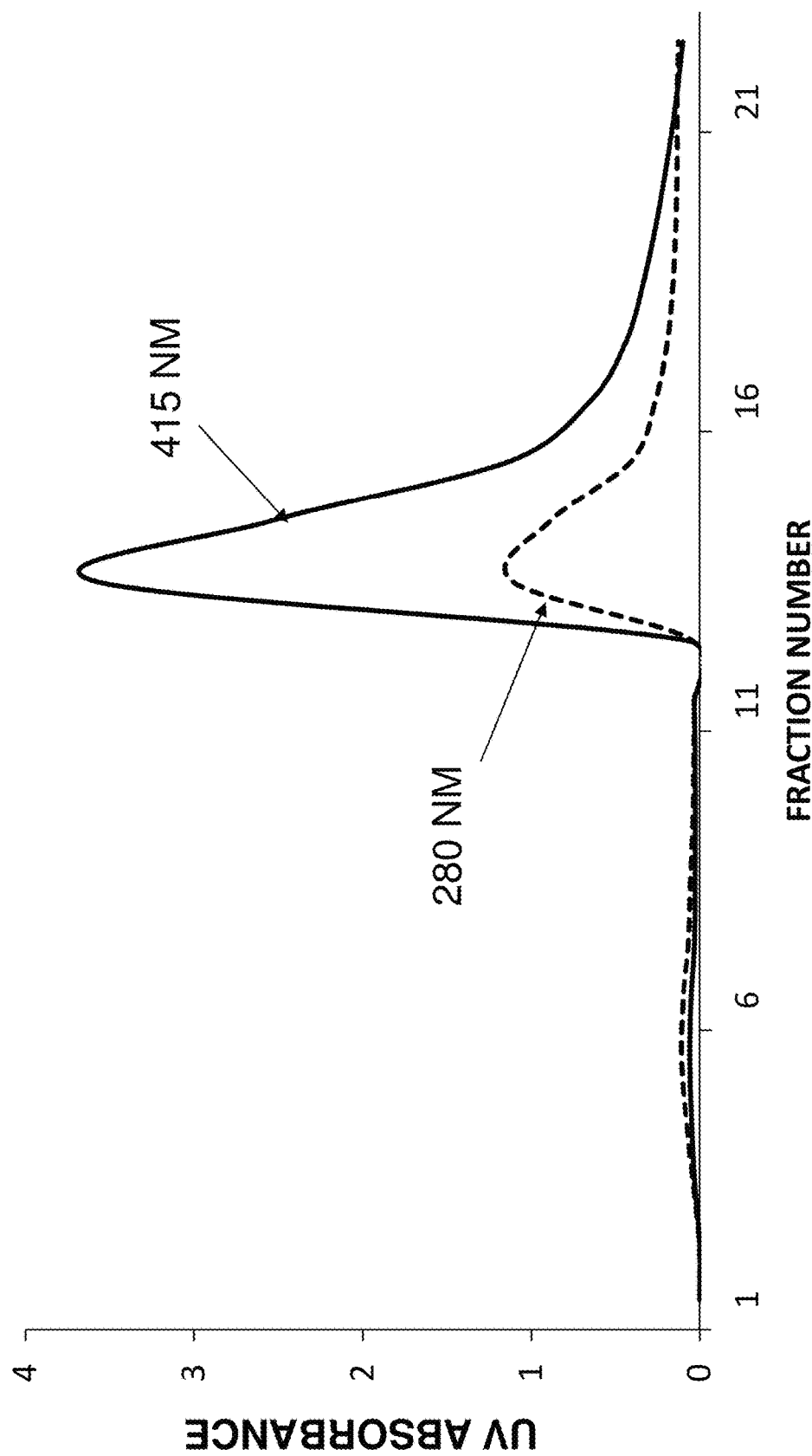
FIG. 5 is an area plot of the composition of the eluate fractions withdrawn from the protein purification process of one embodiment of the invention for purifying heme protein using a strong anion exchange resin.

FIG. 5 shows the optical density area plot of the protein concentrations of the numbered elute fractions withdrawn from the column in Example 3.

Figure 6:
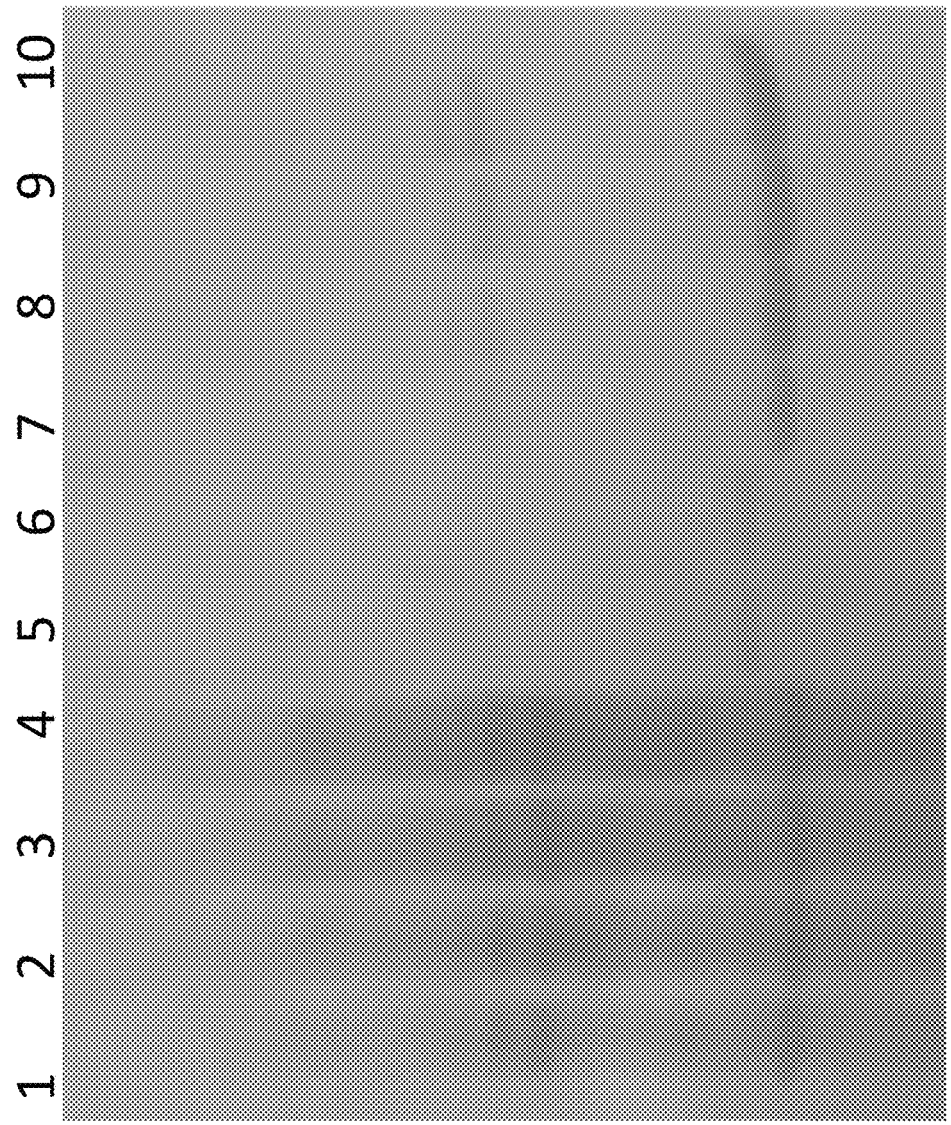
FIG. 6 is a gel electrophoresis result of an SDS-PAGE protein analysis using 4-12% Bis-Tris Gel of the elute fractions produced by one embodiment of the invention for purifying heme protein using a strong anion exchange resin.

FIG. 6 is gel electrophoresis result of an SDS-PAGE protein analysis using 4-12% Bis-Tris Gel of the elute fractions produced in Example 3. FIG. 6 shows the collected elute fractions eluted from the column of Example 3 on 4-12% Bis-Tris SDS-PAGE imager at various points in the SMB process. The results are shown in lanes which are numbered along the x-axis. Lane 1: Lysate 5 ul (microliters); Lane 2: Lysate 6 ul; Lane 3: Lysate 8 ul; Lane 4: Lysate 10 ul; Lane 5: FT 30 ul; Lane 6: Wash 30 ul; Lane 7: Elution pool 10 ul; Lane 8: Elution pool 15 ul; Lane 9: Elution pool 20 ul, 2.21 ug (micrograms) heme protein of interest, and Lane 10: Elute pool 25 ul.

Example 4—Plant (RuBisCO) Protein Purification Using Single Column Purification with Strong Anion Exchange Resin Example 4 represented a single column purification of the plant protein, RuBisCO (1,5-bisphosphate carboxylase/oxygenase) protein from spinach extract. The stationary phase employed in the single column was TOYOPEARL GIGACAP Q-650, a high capacity, high resolution, strong anion exchange resin having a backbone of a hydroxylated polymethacrylate polymer (Available from Tosoh Bioscience LLC, King of Prussia, Pa.). A 5 ml portion (column volume) of the resin was loaded in a column having a diameter of about 12 mm and a length of about 45 mm. The resin was equilibrated by passing 10 column volumes of an equilibration buffer comprising a 40 mM sodium phosphate and 0.1 M sodium chloride solution having a pH of 8.0 at 0.5 ml/min. A 0.5 g/liter crude feed mixture of spinach extract was prepared by admixing the spinach extract in the equilibration buffer. In a loading step, the 2.8 liters of the crude feed mixture was passed through the column or loaded on the resin at a rate of about 10 ml/min. In a washing step, the column was washed with about 40 column volumes of a 40 mM solution of sodium phosphate and 0.15 M sodium chloride having a pH of 8.0 at a rate of 10 ml/min. The protein of interest, RuBisCO, remaining on the resin after the wash step was eluted in an elution step by flushing the column with 20 column volumes of an elution buffer having an elution buffer concentration of 40 mM sodium phosphate and 0.35 M sodium chloride and having a pH of 8.0, and introduced at a rate of 10 ml/min. The protein eluate was collected at 5 ml fractions and stored on ice at a temperature of 4° C. The RuBisCO protein concentration in the collected fractions was determined by Pierce 660 nm protein assay. The Pierce 660 NM Protein Assay (Available from Thermo Fischer Scientific, Pittsburgh, Pa.) uses a proprietary dye-metal complex which binds to protein in acidic conditions, causing a shift in the dye's absorption maximum, which is measured at 280 nm. Purity of the protein was determined by analyzing the collected product fractions on 4-12% Bis-Tris SDS-PAGE followed by densitometry using Bio-Rad's EZ Imager (See FIG. 6). NuPAGE Bis-Tris gels (Available from Thermo Fischer Scientific, Pittsburgh, Pa.) are precast polyacrylamide gels designed to provide separation of small to medium-sized proteins during gel electrophoresis. Bio-Rad's EZ IMAGER is an automated gel imaging instrument (Available from Bio-Rad, Hercules, Calif.). The RuBisCO protein content of the spinach extract was determined by densitometry to contain 7.47 mg of the approximately 34.125 mg loaded. The RuBisCO protein found in the protein product elute fractions (shown in FIG. 6 as Lanes 7-10) was determined to be 5.9 mg. Thus, using the strong basic resin TOYOPEARL GIGACAP Q-650, the RuBisCO protein extraction yield was about 72 percent on a weight basis compared to the amount of RuBisCO protein in the feed, and the RuBisCO protein purity was about 85 wt %, determined by densitometry.

FIG. 7 shows the elution profile of RuBisCO from spinach in an optical density area plot of the protein concentrations of the numbered elute fractions withdrawn from the column in Example 4.

Figure 8:
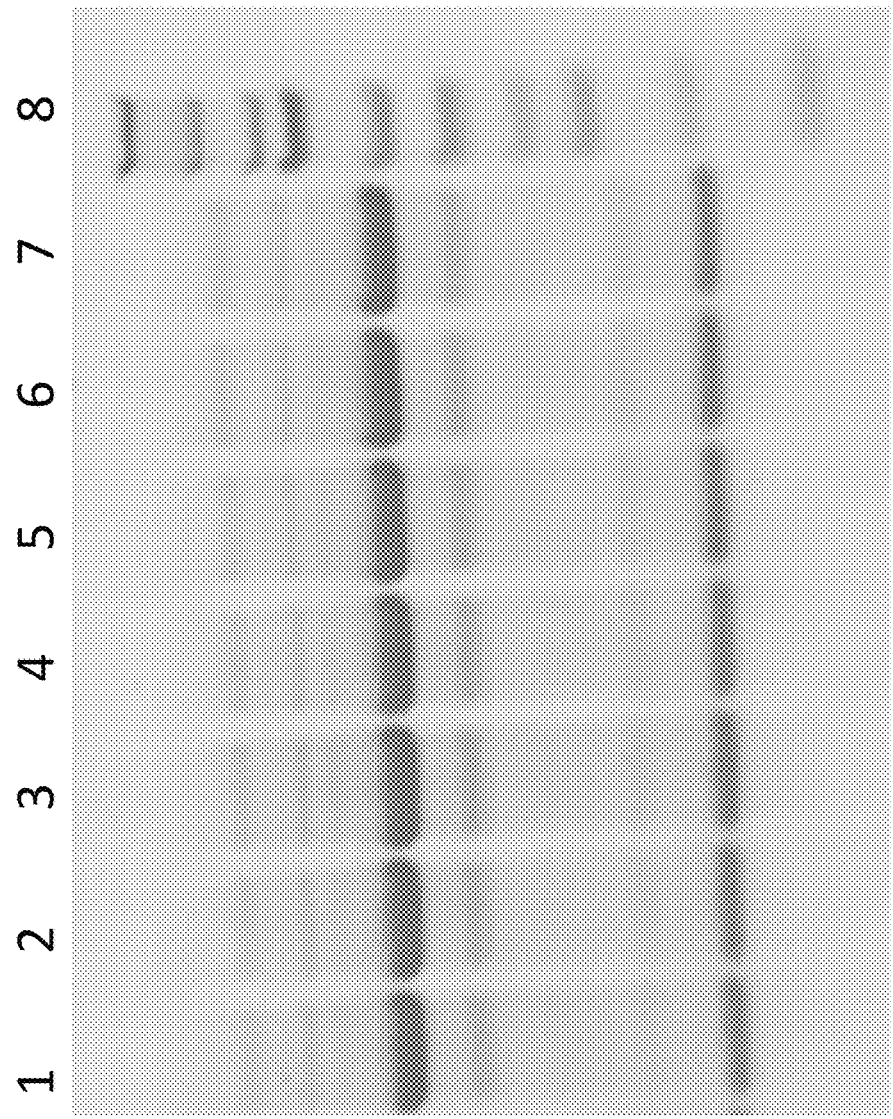
FIG. 8 is a gel electrophoresis result of an SDS-PAGE protein analysis using 4-12% Bis-Tris Gel of the elute fractions for purifying RuBisCO produced by one embodiment of the invention using a strong anion exchange resin.

FIG. 8 is gel electrophoresis result of an SDS-PAGE protein analysis using 4-12% Bis-Tris Gel of the elute fractions produced in Example 4. The results are shown in lanes which are numbered along the x-axis. Lanes 1-7: Purified RuBisCO protein and Lane 8: Molecular weight marker proteins.

Example 5—Pea Protein Purification Using A Single Column Purification with Strong Anion Exchange Resin Example 5 represented a Single Column purification of Pea protein from pea flour. The stationary phase employed in the SMB was TOYOPEARL GIGACAP Q-650, a high capacity, high resolution, strong anion exchange resin having a backbone of a hydroxylated polymethacrylate polymer (Available from Tosoh Bioscience LLC, King of Prussia, Pa.). A 5 ml portion (column volume) of the resin was loaded in a column having a diameter of about 12 mm and a length of about 45 mm. The resin was equilibrated by passing 20 column volumes of an equilibration buffer comprising a 20 mM sodium phosphate and 0.05 M sodium chloride solution having a pH of 8.0 at 2 ml/min. A 1 wt % pea flour SMB feed mixture of the pea flour was prepared by admixing about 1 g/100 ml of the pea flour in the equilibration buffer. The total protein concentration in the crude feed mixture was 5.2 mg/ml as determined by Pierce 660 NM protein assay. In a loading step, the 50 ml of the crude feed mixture was passed through the column or loaded on the resin at a rate of about 2 ml/min. In a washing step, the column was washed with about 5 column volumes of a 20 mM sodium phosphate and 0.05 M sodium chloride solution having a pH of 8.0 at a rate of 2 ml/min. The proteins of interest, 3 target proteins (Group A, B, and C), remaining on the resin after the wash step were eluted in an elution step by flushing the column with 4 column volumes of an elution buffer having a linear gradient of from 50 mM to 500 mM sodium chloride in 20 mM sodium phosphate and having a pH of 8.0 at a rate of 2 ml/min. The protein eluate was collected at 5 ml fractions and stored on ice at a temperature of 4° C. The pea protein concentrations in the collected fractions were determined by Pierce 660 nm protein assay at 280 nm. Purity of the protein was determined by analyzing the collected product fractions on 4-12% Bis-Tris SDS-PAGE followed by densitometry using Bio-Rad's EZ Imager (See FIG. 6). NuPAGE Bis-Tris gels (Available from Thermo Fischer Scientific, Pittsburgh, Pa.) are precast polyacrylamide gels designed to provide separation of small to medium-sized proteins during gel electrophoresis. There were 3 target proteins identified as Target A, Target B, and Target C, The total protein found was as follows: Target group A proteins—51 mg, Target group B proteins—90 mg, and Target group C proteins 5 mg. The proteins in the eluted fractions was determined using a Pierce 660NM protein assay.

Figure 11:
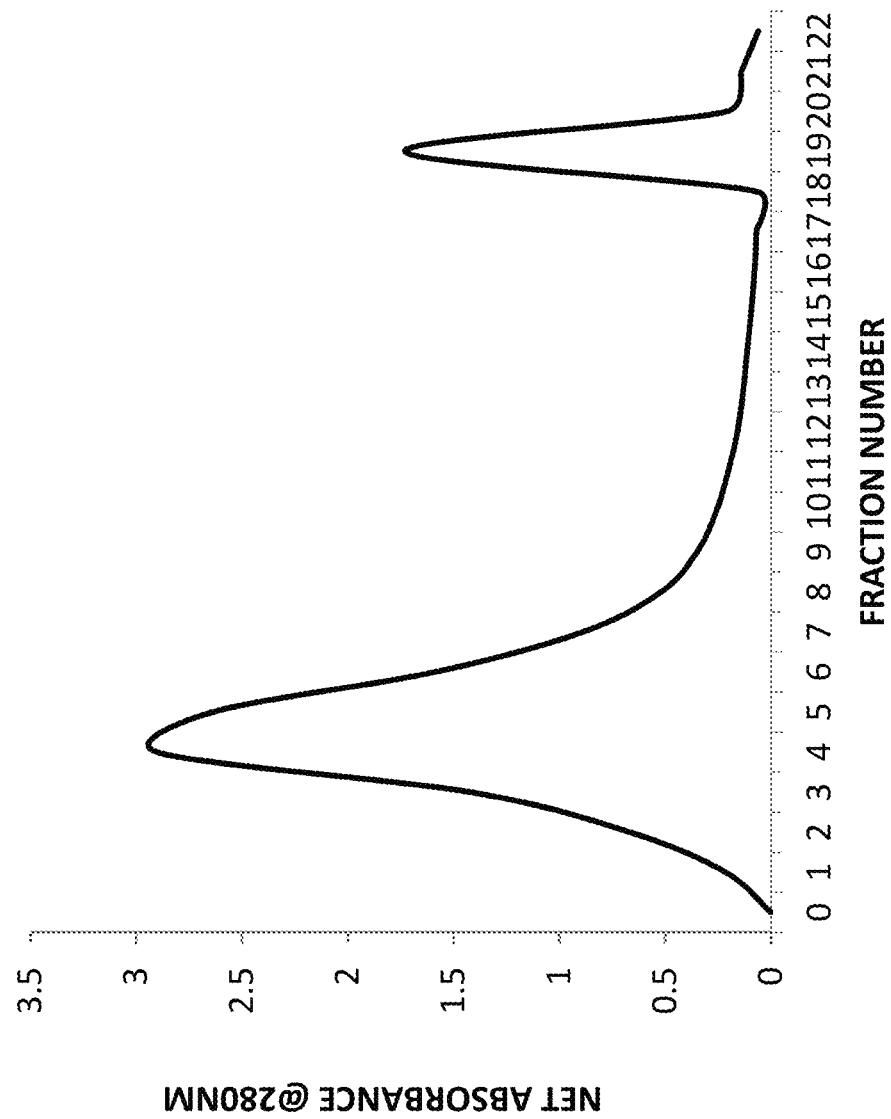
FIG. 11 is an area plot of the composition of the eluate fractions withdrawn from the protein purification process of one embodiment of the invention for purifying pea proteins on a strong anion exchange resin.

FIG. 11 shows the elution profile of pea proteins extracted from pea flour in an optical density area plot (UV Absorbance @280 nm) of the pea protein concentrations of the numbered elute fractions withdrawn from the column in Example 5.

Figure 12:
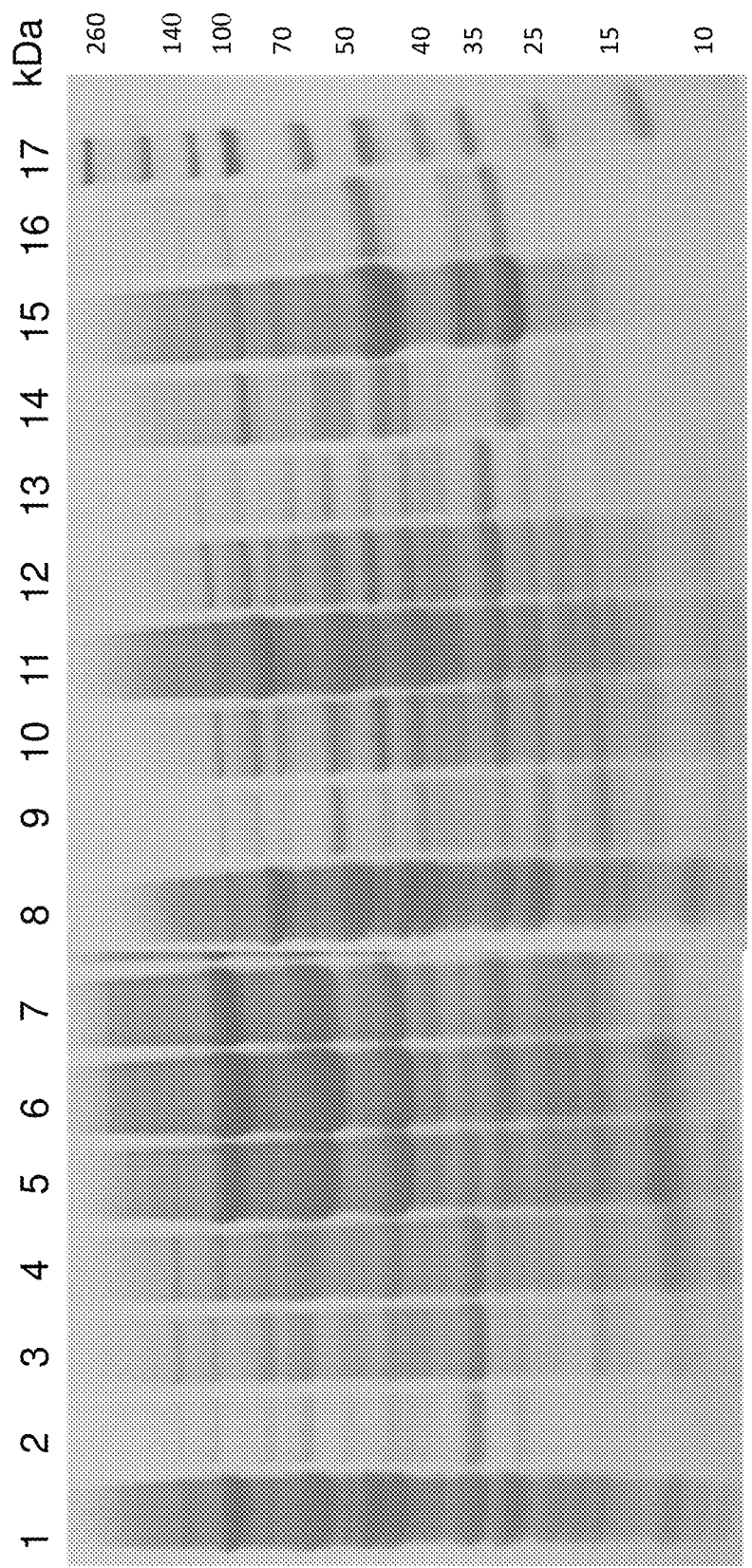
FIG. 12 is a gel electrophoresis result of an SDS-PAGE protein analysis using 4-12% Bis-Tris Gel of the elute fractions for purifying pea proteins produced by one embodiment of the invention using a strong anion exchange resin.

FIG. 12 is gel electrophoresis result of an SDS-PAGE protein analysis using 4-12% Bis-Tris Gel of the elute fractions produced in Example 5. The results are shown in lanes which are numbered along the x-axis. Lanes 2-4 contain Target group A pea proteins, Lanes 5-7 contain Target group B pea proteins, and Lanes 15-16 contain Target group C pea proteins. Lane 17 shows molecular weight marker proteins.

Figure 13:
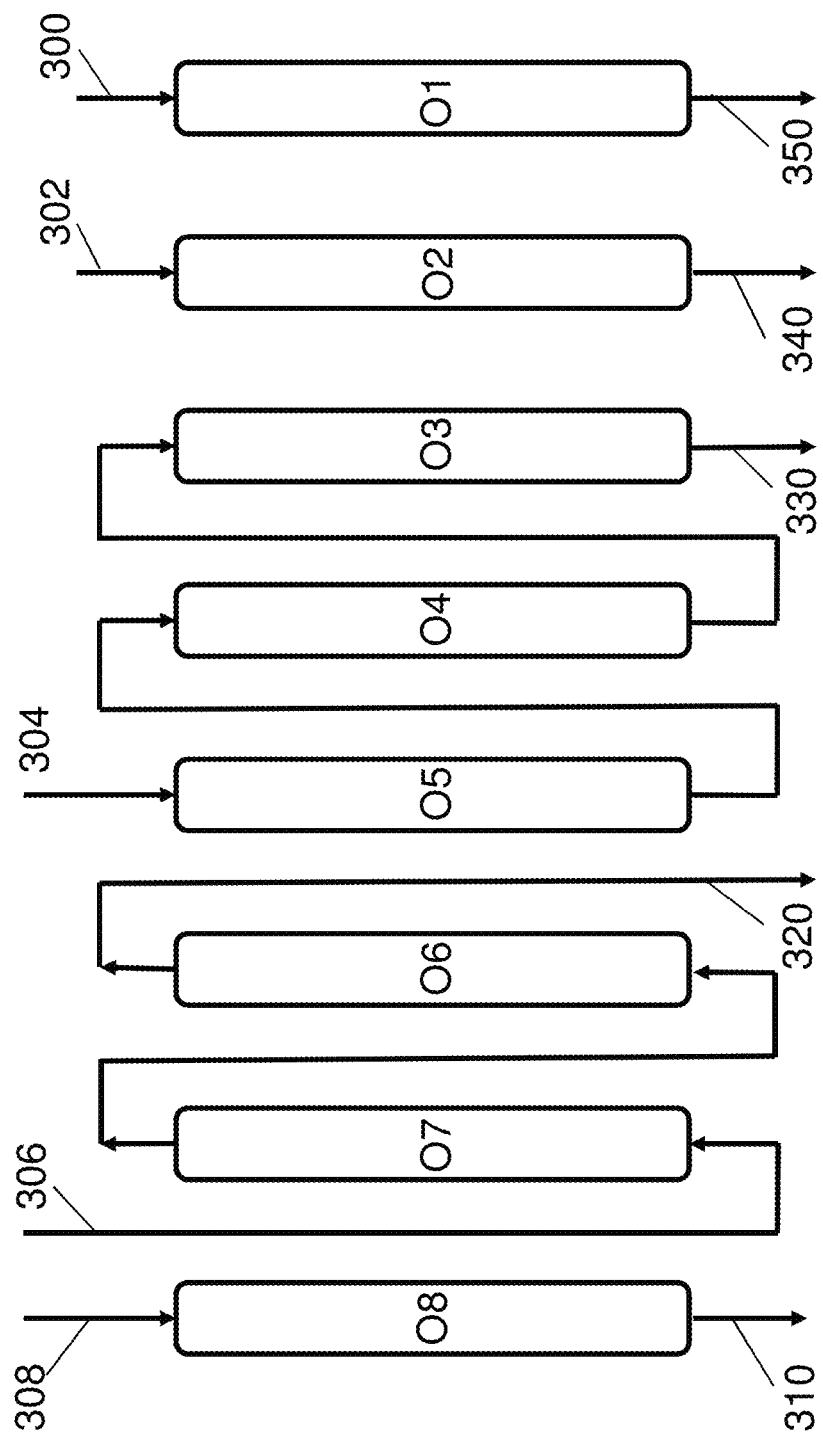
FIG. 13 is a schematic block flow diagram of an 8 bed simulated moving bed process of Example 6 for purification of leghemoglobin.

Example 6—Simulated Moving Bed Purification of Heme Protein in an 8-Bed Simulated Moving Bed Separation Approximately 20 ml of DIAION HPA25L a strongly basic anion exchange resin having a backbone matrix of styrene divinyl benzene polymer (Available from Mitsubishi Chemical Company, Tokyo, Japan) was loaded in each of eight 20 ml cartridges. Each cartridge was a vertical column having a diameter of 21 mm and a height of 80 mm. Each of the cartridges were prepared by passing about 30 column volumes of an equilibration buffer comprising 5 mM of potassium phosphate at a pH of 8.0 at a rate of 20 ml/min. The yeast lysate to be purified was kept frozen. A 200 ml portion of the frozen yeast lysate was thawed at room temperature (25° C.) and diluted to a volume of 650 ml by the addition of the equilibration buffer to provide a crude feed mixture. The crude feed mixture pH was adjusted to 8.0 by the addition of a sufficient amount of a 1N solution of sodium hydroxide. The crude feed was maintained at a feed temperature of about 4° C. with ice. The conductivity of the crude feed mixture was about 0.9 mS/cm. A bench scale OCTAVE simulated moving bed unit (Available from Semba Biosciences, Inc., Madison, Wis.) was configured with eight beds according to the process flow of FIG. 13. The SMB process took place at room temperature and atmospheric pressure, but the feed mixture and the eluted product streams were maintained at a temperature of about 4° C. on ice. According to FIG. 13, the crude feed mixture was introduced in line 300 to load adsorbent bed O1 (loading zone) and a first waste stream is withdrawn in line 350. A wash buffer is introduced to adsorbent bed O2 (wash zone) in line 302 and a second wash stream is withdrawn from adsorbent bed O2 in line 340. An elution buffer in line 304 is introduced to adsorbent bed O5 which is in serial fluid communication with adsorbent beds O4 and O3 (elution zone O5-O3) and a product stream is withdrawn from adsorbent bed O3 in line 300. Adsorbent beds O7 and O6 (regeneration zone) are counter currently regenerated in line 306 by passing a first regeneration buffer to the bottom of regeneration bed O7 which is in serial fluid communication with adsorbent bed O6 and a third waste stream is withdrawn from adsorbent bed O6 in line 320. A second regeneration buffer and a first equilibration buffer are also introduced in line 306 to complete the regeneration process and initiate the equilibration process at the appropriate point in the SMB cycle. The second equilibration buffer is introduced in line 308 to adsorbent bed O8 (equilibration zone) and a fourth waste stream is withdrawn in line 310. The crude feed rate was 2 ml/ml. The wash buffer comprised 5 column volumes of 5 mM potassium phosphate at a pH of 8.0 and was introduced at a rate of 2 ml/min. The elution step comprised passing an elution buffer of 10 column volumes of 5 mM potassium phosphate and 50 mM sodium chloride at a rate of 2 ml/min. The regeneration step comprised passing 5 column volumes of a first regeneration buffer of 2 M sodium hydroxide and 1 M sodium chloride and a rate of 1.66 ml/min, followed by passing a second regeneration buffer of 5 column volumes of 1% HCl at 20 ml/min, followed by passing a first equilibration buffer of 5 column volumes of 50 mM potassium phosphate having a pH of 8.0 at a rate of 20 ml/min. The second equilibration buffer of 30 column volumes of 5 mM potassium phosphate and having a pH of 8.0 was passed to O8 in line 308 at a rate of 20 ml/min. The elute product stream in line 330 was monitored at a UV wave length of 280 NM and the protein concentration was determined by a Pierce 660 NM protein assay. The purity of the elute product was determined by analyzing the eluted fractions on a 4-12% Bis-Tris SDS-Page followed by densitometry using a Bio-Rad's Gel Doc EZ Imager as described hereinabove. The total amount of protein in the crude feed mixture was 1120 mg. The protein of interest, leghemoglobin, was determined to be 26 wt % by densitometry and equal to 291 mg. The SMB product eluted from the SMB was 301.6 mg and the purity of the SMB product was determined by densitometry to be 80 wt %. Thus, the amount of pure (100%) leghemoglobin in the product was 241 mg, and the overall yield of the leghemoglobin was 83 wt %, based on the amount of leghemoglobin in the crude feed mixture.

While the disclosure has been described in terms of specific embodiments, it is evident in view of the foregoing description that numerous alternatives, modifications and variations will be apparent to those skilled in the art. Accordingly, the disclosure is intended to encompass all such alternatives, modifications and variations which fall within the scope and spirit of the disclosure and the following claims.

Figure 14:
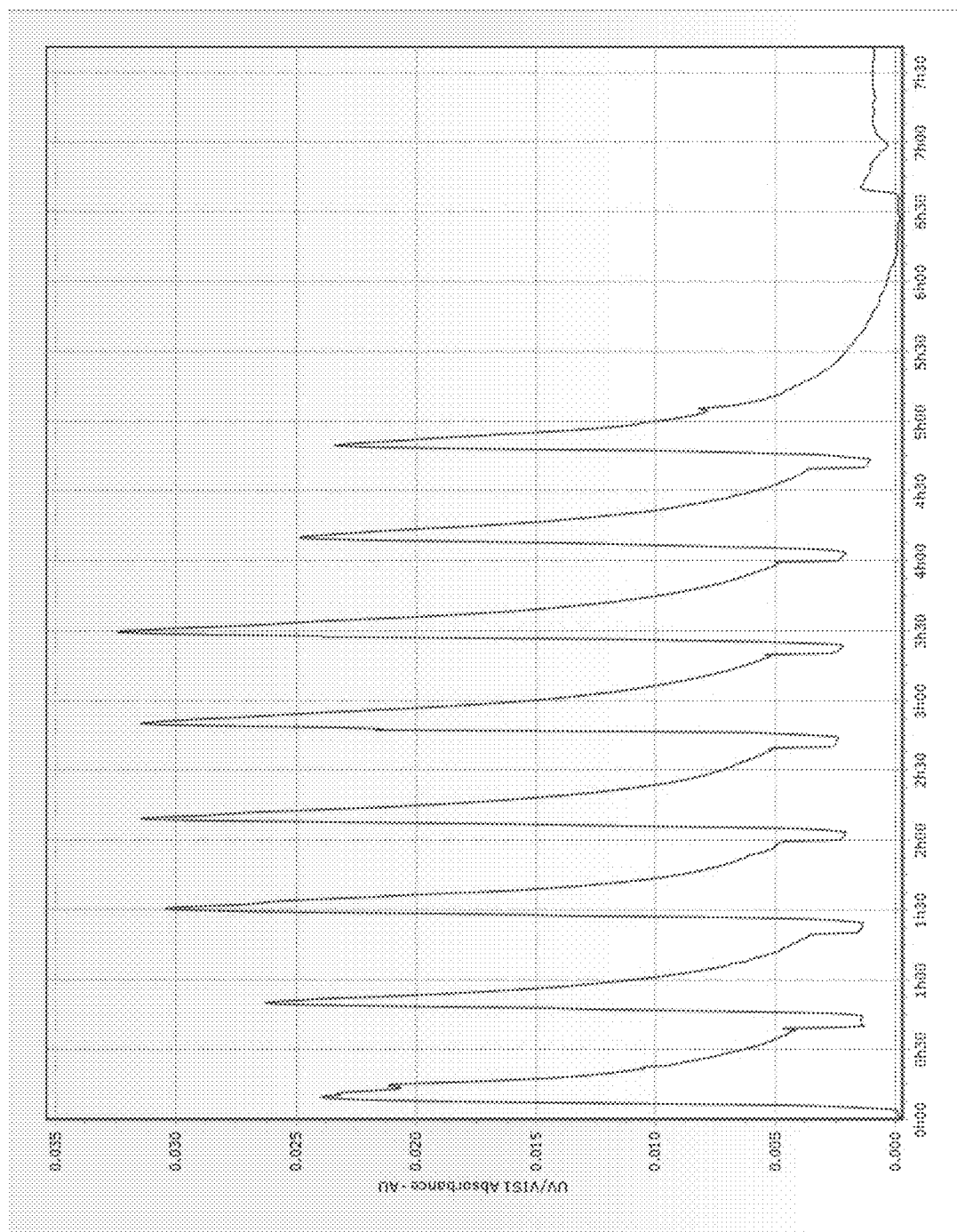
FIG. 14 shows the optical density of the elute fractions withdrawn from the Simulated Moving Bed process in Example 6.

FIG. 14 shows the optical density of the elute fractions withdrawn from the Simulated Moving Bed process in Example 6.

FIG. 15 is gel electrophoresis result of an SDS-PAGE protein analysis using 4-12% Bis-Tris Gel of the elute fractions produced in Example 6. FIG. 14 shows the collected elute fractions eluted from the column of Example 6 on 4-12% Bis-Tris SDS-PAGE imager at various points in the SMB process. The results are shown in lanes which are numbered along the x-axis. Lane 1: Lysate 5 μl; Lane 2: Lysate 10 ul, Lane 3: Flowthrough 30 ul; Lane 4: Wash 30 ul; Lane 5: Elute Pool 10 ul; Lane 6: Elute Pool: 25 μl; Lane 7: Elute Pool 15 ul; Lane 8: Molecular weight marker Proteins.

We claim:

1. An adsorbent for use in chromatographic separation and extraction of protein, said adsorbent comprising a microcrystalline cellulose which has been cross linked with epichlorohydrin and reacted with 2,3-epoxypropyltrimethylammonium chloride, wherein said adsorbent is present in a plurality of adsorbent beds configured in a simulated moving bed arrangement.

2. The adsorbent of claim 1, wherein the adsorbent has a particle size ranging from about 150 to about 250 microns.

3. The adsorbent of claim 1, wherein the adsorbent has a loose bulk density of from about 0.29 to about 0.39 g/cc.

4. An adsorbent for use in chromatographic separation and extraction of protein, said adsorbent comprising a microcrystalline cellulose which has been cross linked with epichlorohydrin and reacted with 2,3-epoxypropyltrimethylammonium chloride having a particle size ranging from about 150 to about 250 microns and a loose bulk density of from about 0.29 to about 0.39 g/cc, wherein said adsorbent is present in a plurality of adsorbent beds configured in a simulated moving bed arrangement.

5. The adsorbent of claim 1, wherein the adsorbent has an average particle size of about 180 microns.

6. The adsorbent of claim 1, wherein the adsorbent has a moisture content of 2 to 5 wt. %.

7. The adsorbent of claim 2, wherein the adsorbent has an average particle size of about 180 microns.

8. The adsorbent of claim 2, wherein the adsorbent has a moisture content of 2 to 5 wt. %.

9. The adsorbent of claim 3, wherein the adsorbent has an average particle size of about 180 microns.

10. The adsorbent of claim 3, wherein the adsorbent has a moisture content of 2 to 5 wt. %.

11. The adsorbent of claim 4, wherein the adsorbent has an average particle size of about 180 microns.

12. The adsorbent of claim 4, wherein the adsorbent has a moisture content of 2 to 5 wt. %.

* * * * *